US010792366B2

United States Patent
Ho et al.

(10) Patent No.: US 10,792,366 B2
(45) Date of Patent: Oct. 6, 2020

(54) METHODS TO REDUCE TOXICITIES AND TO IMPROVE BIOAVAILABILITIES OF NANODRUGS

(71) Applicant: CARNEGIE MELLON UNIVERSITY, Pittsburgh, PA (US)

(72) Inventors: Chien Ho, Pittsburgh, PA (US); Li Liu, Pittsburgh, PA (US); Qing Ye, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 0 days.

(21) Appl. No.: 15/552,119

(22) PCT Filed: Feb. 18, 2016

(86) PCT No.: PCT/US2016/018446
§ 371 (c)(1),
(2) Date: Aug. 18, 2017

(87) PCT Pub. No.: WO2016/134134
PCT Pub. Date: Aug. 25, 2016

(65) Prior Publication Data
US 2018/0333497 A1 Nov. 22, 2018

Related U.S. Application Data

(60) Provisional application No. 62/176,481, filed on Feb. 19, 2015.

(51) Int. Cl.
A61K 47/44 (2017.01)
A61P 35/00 (2006.01)
(Continued)

(52) U.S. Cl.
CPC ............ A61K 47/44 (2013.01); A23L 33/115 (2016.08); A23L 33/30 (2016.08); A61K 9/0019 (2013.01);
(Continued)

(58) Field of Classification Search
None
See application file for complete search history.

(56) References Cited

U.S. PATENT DOCUMENTS 10,413,509 B2 * 9/2019 Pottier ................. A61K 31/704
2008/0193372 A1 * 8/2008 Lanza ................. A61K 9/1075
424/1.11
(Continued)

FOREIGN PATENT DOCUMENTS

WO WO-2005086639 A2 * 9/2005 ........... A61K 9/1075
WO WO 2014/039874 3/2014
(Continued)

OTHER PUBLICATIONS

RM Abra, ME Bosworth, CA Hunt. "Liposome Disposition In Vivo: Effects of Pre-Dosing With Liposomes." Research Communications in Chemical Pathology and Pharmacology, vol. 29 No. 2, Aug. 1980, pp. 349-360. (Year: 1980).*
(Continued)

Primary Examiner — Isaac Shomer
(74) Attorney, Agent, or Firm — Fish & Richardson P.C.

(57) ABSTRACT

Provided herein are methods for reducing clearance of nanotherapeutic agents from a subject, wherein the methods comprise administering a nutrition supplement to the subject prior to administration of the nanotherapeutic agent in the treatment of a disease. Methods for improving the bioavailability of the nanotherapeutic agent, methods of reducing the
(Continued)

toxicity of the nanotherapeutic agent, and kits comprising the nutrition supplement and nanotherapeutic agent are also provided.

13 Claims, 5 Drawing Sheets

(51) Int. Cl.
    *A61K 9/107*     (2006.01)
    *A61K 31/282*     (2006.01)
    *A61K 9/00*     (2006.01)
    *A61K 9/51*     (2006.01)
    *A61K 9/19*     (2006.01)
    *A23L 33/00*     (2016.01)
    *A23L 33/115*     (2016.01)

(52) U.S. Cl.
    CPC ............... *A61K 9/107* (2013.01); *A61K 9/19* (2013.01); *A61K 9/5161* (2013.01); *A61K 31/282* (2013.01); *A61P 35/00* (2018.01); *A23V 2002/00* (2013.01); *Y10S 977/773* (2013.01); *Y10S 977/906* (2013.01)

(56) References Cited

U.S. PATENT DOCUMENTS

| | | |
|---|---|---|
| 2008/0193374 A1 | 8/2008 | Larsen et al. |
| 2011/0027348 A1 | 2/2011 | Feher |
| 2011/0117192 A1 | 5/2011 | Navon et al. |
| 2014/0274988 A1 | 9/2014 | Lippard et al. |

FOREIGN PATENT DOCUMENTS

| | | | | |
|---|---|---|---|---|
| WO | WO-2014039874 A2 * | 3/2014 | ......... | A61K 49/1827 |
| WO | WO 2014/099056 | 6/2014 | | |
| WO | WO-2014191569 A1 * | 12/2014 | ........... | A61K 31/704 |
| WO | WO 2016/134134 | 8/2016 | | |

OTHER PUBLICATIONS

H Cabral, N Hishiyama, S Okazaki, H Koyama, K Kataoka. "Preparation and biological properties of dichloro(1,2-diaminocyclohexane)platinum(II) (DACHPt)-loaded polymeric micelles." Journal of Controlled Release, vol. 101, 2005, pp. 223-232. (Year: 2005).*
J Huang et al. "Biodegradable self-assembled nanoparticles of poly (D,L-lactide-coglycolide)/hyaluronic acid block copolymers for targeted delivery of docetaxel to breast cancer." Biomaterials, vol. 35, 2014, pp. 550-566, available online Oct. 15, 2013. (Year: 2013).*
Food and Drug Administration. "Intralipid 20". Obtained from https://www.accessdata.fda.gov/drugsatfda_docs/label/2007/017643s072,018449s039lbl.pdf on Feb. 25, 2019, pp. 3-20. (Year: 2019).*
Food and Drug Administration. https://www.accessdata.fda.gov/drugsatfda_docs/label/2007/017643s072,018449s039lbl.pdf accessed Sep. 9, 2019, pp. 3-20. (Year: 2019).*
Albanese et al., "The effect of nanoparticle size, shape, and surface chemistry on biological systems," Annu. Rev. Biomed. Eng. 2012, 14, 1-16.
Alexis et al., "Factors Affecting the Clearance and Biodistribution of Polymeric Nanoparticles," Mol. Pharm. 2008, 5, 505-515.
Arumugam, et al. "Toll-like receptors in ischemia-reperfusion injury," Shock, 32(1):4-16 (2009).
Arvizo et al., "Modulating pharmacokinetics, tumor uptake and biodistribution by engineered nanoparticles," PLoS One, 6(9):e24374 (2011).
Asahina Y, Izumi N, Uchiham M, Noguchi O, Ueda K, Inoue K, Nishimura Y, Tsuchiya K, Hamano K, Itakura J, Himeno Y, Koike M, Miyake S. Assessment of kupffer cells by ferumoxides-enhanced mr imaging is beneficial for diagnosis of hepatocellular carcinoma: Comparison of pathological diagnosis and perfusion patterns assessed by ct hepatic arteriography and ct arterioportography. *Hepatol Res.* 2003;27:196-204.
Barua et al., "Particle shape enhances specificity of antibody-displaying nanparticles," PNAS 110(9):3270-5 (2013).
Bopassa JC, "Protection of the ischemic myocardium during the reperfusion: between hope and reality," Am. J. Cardiovas. Dis., 2(3):223-236 (2012).
Bulte and Kraitchman, "Iron oxide MR contrast agents for molecular and cellular imaging," NMR Biomed., 17(7):484-499 (2004).
Cabral et al., "Targeted therapy of spontaneous murine pancreatic tumors by polymeric micelles prolongs survival and prevents peritoneal metastasis," PNAS, 2013, 110(28):11397-11402.
Cabral H. et al., "Preparation and biological properties of dichloro (1,2-diaminocyclohexane)platinum(III) (DACHPt)-loaded polymeric micelles," J Control Release, 2005, 101(1-3):223-32.
Chan et al., "Ischaemia-reperfusion is an event triggered by immune complexes and complement," Br. J. Surg., 90(12):1470-1478 (2003).
Chauhan et al., "Strategies for advancing cancer nanomedicine," Nat. Mater, 2013, 12(11):958-962.
Chih-Lung Chen et al., "A New Nano-sized Iron Oxide Particle with High Sensitivity for Cellular Magnetic Resonance Imaging", *Mol Imaging Biol.* 2011;13(5):825-839.
Cho NH, Cheong TC, Min JH, Wu JH, Lee SJ, Kim D, Yang JS, Kim S, Kim YK, Seong SY. A multifunctional core-shell nanoparticle for dendritic cell-based cancer immunotherapy. *Nat Nanotechnol.* 2011;6:675-682.
Chouly et al., "Development of superparamagnetic nanoparticles for MRI: effect of particle size, charge and surface nature on biodistribution," J. Microencapsulation, 13(3):245-255 (1996).
Chow and Dean Ho, "Cancer Nanomedicine: From Drug Delivery to Imaging," Sci. Trans. Med. 2013, 5, 216rv214, pp. 1-13.
Clement JH, Schwalbe M, Buske N, Wagner K, Schnabelrauch M, Gornert P, Kliche KO, Pachmann K, Weitschies W, Hoffken K. Differential interaction of magnetic nanoparticles with tumor cells and peripheral blood cells. *J Cancer Res Clin Oncol.* 2006;132:287-292.
Del Frate C, Bazzocchi M, Mortele KJ, Zuiani C, Londero V, Como G, Zanardi R, Ros PR. Detection of liver metastases: Comparison of gadobenate dimeglumine-enhanced and ferumoxides-enhanced mr imaging examinations. *Radiology.* 2002;225:766-772.
Edwards et al., "Metabolomics reveals increased isoleukotoxin diol (12, 13-DHOME) in human plasma after acute Intralipid infusion," J. Lipid Res. 53(9):1979-1986 (2012).
EP Search Report in corresponding Application No. 16753050.0, dated Jan. 30, 2019, pages.
Epelman and Mann, "Communication in the heart: the role of the innate immune system in coordinating cellular responses to ischemic injury," J. Cardiovas. Transl. Res., 5(6):827-3 (2012).
Esteban-Fernandez et al., "Accumulation, fractionation, and analysis of platinum in toxicologically affected tissues after cisplatin, oxaliplatin, and carboplatin administration," Journal of Analytical Toxicology 2008, 32(2):140-146.
Fraser I et al., "The intravenous intralipid tolerance test," J Leukoc Biol. 1984, 36(5):647-9.
Granot et al., "Serial Monitoring of Endogenous Neuroblast Migration by Cellular MRI", *Neuroimage.* 2011;57(3):817-824.
Harvery and Cave, "Intralipid infusion ameliorates propranolol-induced hypotension in rabbits," J. Med. Toxicol., 4(2):71-76 (2008).
Haxton et al., "Polymeric Drug Delivery of Platinum-Based Anticancer Agents," Jul. 2009, Journal of Pharmaceutical Sciences, vol. 98(7):2299-2316.
Heger et al., "Amgen deal triggers watchful waiting in targeted nanomedicine," Nat. Med. 2013, 19, 120.
Heidenreich, et al. "Forecasting the future of cardiovascular disease in the United States: a policy statement from the American Heart Association," Circulation 123(8):933-944 (2011).
Ho C, Hitchens TK. A non-invasive approach to detecting organ rejection by MRI: Monitoring the accumulation of immune cells at the transplanted organ. *Curr Pharm Biotechnol.* 2004;5:551-566.
Ho, "A Novel Approach to Improve the Delivery and Reduce the Toxic Side Effects of Anticancer Nanodrugs by Treatment with

(56) References Cited

OTHER PUBLICATIONS

Intralipid," 2014 Projects: Disruptive Healthcare Technology Insitute (DHTI) at Carnagie Mellon University, Jan. 1, 2014 (Jan. 1, 2014), XPO55534631, Retrieved from Internet: URL: http://www.dhti.cmu.edu/dhti/projects-2014.asp.
Http://www.Bangslabs.Com/sites/default/files/bangs/docs/pdf/pds_731.Pdf.
Hu et al., "Assembly of Nanoparticle—Protein Binding Complexes: From Monomers to Ordered Arrays," Angewandte Chem Int. Ed. Engl, 46(27):5111-5114 (2007).
Hu et al., "Nanoparticle-assisted combination therapies for effective cancer treatment," Therapeutic Delivery 1(2):323-34 (2010).
Ito A, Tanaka K, Kondo K, Shinkai M, Honda H, Matsumoto K, Saida T, Kobayashi T. Tumor regression by combined immunotherapy and hyperthermia using magnetic nanoparticles in an experimental subcutaneous murine melanoma. Cancer Sci. 2003;94:308-313.
Jarstrand et al., "Human granulocyte and reticuloendothelial system function during intralipid infusion," 1978 JPEN J. Parenter. Enteral. Nutr. 2:663-670.
Jarzyna et al., "Iron oxide core oil-in-water emulsions as a multi-functional nanoparticle platform for tumor targeting and imaging," 2009 Biomaterials 30:6947-6954.
Jokerst et al., "Nanoparticle PEGylation for imaging and therapy," Nanomedicine (Lond), 2011, 6(4):715-728.
Kievit FM, Zhang M. "Surface engineering of iron oxide nanoparticles for targeted cancer therapy", Acc Chem Res. 2011;44(10):853-862.
Kinsey et al., "Regulatory T cells contribute to the protective effect of ischemic preconditioning in the kidney," Kidney International, 77(9):771-780 (2010).
Knight et al., "Cold ischemic injury, aortic allograft vasculopathy, and pro-inflammatory cytokine expression," J. Surg. Res. 113(2):201-207 (2003).
Kosieradzki and Rowinski, "Ischemia/reperfusion injury in kidney transplantation: mechanisms and prevention," Transplant Proc., 40(10):3279-3288 (2008).
Kraitchman et al., "MR Imaging of Transplanted Stem Cells in Myocardial Infarction", *Methods Mol Biol*. 2011;680:141-152.
Krogh-Madsen, et al. "Effect of short-term intralipid infusion on the immune response during low-dose endotoxemia in humans," Am J. Physiol. Endocrinol. Metab., 294(2):E371-379 (2008).
Laroui et al., "Gastrointestinal Delivery of Anti-Inflammatory Nanoparticles," Methods in Enzymology, 509:101-25 (2012).
Li et al., "Intralipid, a Clinically Safe Compound, Protects the Heart Against Ischemia-Reperfusion Injury More Efficiently Than Cyclosporine-A," NIH Public Access, Anesthesiology, Oct. 2012; 117(4):1-22.
Liu et al., "A New Approach to Reduce Toxicities and to Improve Bioavailabilities of Platinum-Containing Anti-Cancer Nanodrugs," Sci. Rep. 2015, 5, 10881.
Liu et al., "Decreased reticuloendothelial system clearance and increased blood half-life and immune cell labeling for nano- and micron-sized superparamagnetic iron-oxide particles upon pre-treatment with Intralipid," Biochim. Biophys. Acta. 2013, 1830,(6):3447-3453.
Liu L, Ye, Q, Wu, YL, Hsieh, W, Chen, C, Shen, H, Wang, SJ, Zhang, H, Hitchens, TK, Ho, C. Tracking t-cells in vivo with a new nano-sized MRI contrast agent. *Nanomedicine: Nanotechnology, Biology, and Medicine*, doi:10.1016/j.nano.2012.02.017. . 2012.
Lou et al., The Mechanism of Intralipid-Mediated Cardioprotection Complex IV Inhibition by the Active Metabolite, Palmitoylcarnitine, Generates Reactive Oxygen Species and Activates Reperfusion Injury Salvage Kinases, PLOS One, Jan. 2014; 9(1):e87205, pp. 1-13.
Lutz et al., "Anti-inflammatory treatment strategies for ischemia/reperfusion injury in transplantation," J. Inflamm (Lond), 7:27 (2010).
Maesaki, "Drug Delivery System of Anti-Fungal and Parasitic Agents," Current Pharmaceutical Design, 8(6):433-440 (2002).
Murakami et al., "Improving drug potency and efficacy by nanocarrier-mediated subcellular targeting," Sci. Trans. Med. 2011, 3, 64ra62.

Nahas et al., "Role of growth hormone in the development of experimental renal scarring," Kidney Int., 40(1):29-34 (1991).
Neuberger, et al., "Superparamagnetic nanoparticles for biomedical applications: Possibilities and limitations of a new drug delivery system," Journal of Magnetism and Magnetic Materials, 293:483-496 (2005).
Nugent, "Intralipid Effects on Reticuloendothelial Function," Journal of Leukocyte Biology 36(2):123-132 (1984).
Oberoi et al., "Preparation and In Vivo Evaluation of Dichloro(1,2-Diaminocyclohexane)platinum(II)-Loaded Core Cross-Linked Polymer Micelles," Chemother. Res. Pract. 2012, 905796.
Oberoi Hardeep S. et al., "Nanocarriers for delivery of platinum anticancer drugs," Advanced Drug Delivery Reviews:65(13):1667-1685 (2013).
Okon et al., "Biodegradation of Magnetite Dextran Nanoparticles in the Rat, A Histologic and Biophysical Study," Laboratory Investigation, 71(6):895-903 (1994) [Abstract Only].
PCT International Search Report for corresponding PCT Application No. PCT/US16/18446 dated May 3, 2016, pp. 1-34.
Prosch H, Oschatz E, Pertusini E, Mostbeck G. Diagnosis of thoracic splenosis by ferumoxides-enhanced magnetic resonance imaging. *J Thorac Imaging*. 2006;21:235-237.
Rahman et al., "Phosphorylation of GSK-3β mediates Intralipid-induced cardioprotection against Ischemia/Reperfusion injury," NIH Public Access Anesthesiology. Aug. 2011; 115(2):1-25.
Rodriguez et al., Minimal "Self" peptides that inhibit phagocytic clearance and enhance delivery of nanoparticles, Science 339(6122):971-975 (2013).
Romberg et al., "Sheddable coatings for long-circulating nanoparticles," Pharm Res. 25(1):55-71 (2008).
Rosi et al., "Oligonucleotide-Modified Gold Nanoparticles for Intracellular Gene Regulation," Science 312:1027-1030 (2006).
Shapiro et al., "MRI detection of single particles for cellular imaging", *Proc Natl Acad Sci USA*. 2004;101(30):10901-10906.
Simberg et al., "Biomimetic amplification of nanoparticle homing to tumors," 2007 PNAS, 104:932-936.
Siqueira et al., "Substitution of Standard Soybean Oil with Olive Oil-Based Lipid Emulsion in Parenteral Nutrition: Comparison of Vascular, Metabolic, and Inflammatory Effects," J. Clin. Endocr. Metab., 2011, vol. 96(10):3207-3216.
Solez, K. et al., "The morphology of "acute tubular necrosis" in man: analysis of 57 renal biopsies and a comparison with the glycerol model," Medicine 58:362-376 (1979).
Stewart et al., "Revision of the 1990 working formulation for the standardization of nomenclature in the diagnosis of heart rejection," J. Heart Lung Transplant, 24(11):1710-1720 (2005).
Sumner et al., In Vivo Labeling of Adult Neural Progenitors for MRI with Micron Sized Particles of Iron Oxide: Quantification of Labeled Cell Phenotype. *Neuroimage*. 2009;44(3):671-678.
Tanaka et al., "Prolonged cold ischemia in rat cardiac allografts promotes ischemia-reperfusion injury and the development of graft coronary artery disease in a linear fashion," J. Heart Lung Transplant, 24(11):1906-1914 (2005).
Tang et al., "On the Use of Micron-Sized Iron Oxide Particles (MPIOS) to Label Resting Monocytes in Bone Marrow", *Mol Imaging Biol*. 2011;13(5):819-824.
Thu et al., "Self-assembling nanocomplexes by combining ferumoxytol, heparin and protamine for cell tracking by magnetic resonance imaging," Nat. Med. 2012, 18(3):463-467.
Van de Werf, et al., "Management of acute myocardial infarction in patients presenting with persistent ST-segment elevation: the Task Force on the Management of ST-Segment Elevation Acute Myocardial Infarction of the European Society of Cardiology," Eur. Heart J., 29(23):2909-2945 (2008).
Velasquez et al., "Perindopril ameliorates glomerular and renal tubulointerstitial injury in the SHR/N-corpulent rat," Hypertension, 30(5):1232-1237 (1997).
Vilaro and Llobera, "Uptake and metabolism of Intralipid by rat liver: an electron-microscopic study," J. Nutr. 118(8):932-940 (1988).
Wang et al., "Nanoparticle delivery of cancer drugs," Annu Rev Med, 2012, 63:185-198.
Wang, M.D., "Biofunctionalized Targeted Nanoparticles for Therapeutic Applications", *Expert Opin Biol Ther*. 2008;8(8):1063-1070.

(56) References Cited

OTHER PUBLICATIONS

Wanten and Calder, "Immune modulation by parenteral lipid emulsions," Am. J. Clin. Nutr. 85(5):1171-1184 (2007).
Winter et al., "The international society for heart and lung transplantation grading system for heart transplant biopsy specimens: Clarification and commentary," J. Heart Lung Transplant, 17:754-760 (1998).
Wu et al., "In situ labeling of immune cells with iron oxide particles: an approach to detect organ rejection by cellular MRI," PNAS 103(6):1852-1857 (2006).
Wu et al., "MRI investigations of graft rejection following organ transplantation using rodent models," Method Enzymol. 386:73-105 (2004).
Wu et al., "Noninvasive evaluation of cardiac allograft rejection by cellular and functional cardiac magnetic resonance," JACC Cardiovasc Imaging, 2(6):731-741 (2009).
Wu YL, Ye, Q. & Ho, C. Cellular and functional imaging of cardiac transplant rejection. *Current Cardiovascular Imaging Reports.* 2011;4:50-26.
Yang et al., "Single chain epidermal growth factor receptor antibody conjugated nanoparticles for in vivo tumor targeting and imaging," Small, 5(2):235-43 (2009).
Ye et al., "In vivo detection of acute rat renal allograft rejection by MRI with USPIO particles," Kidney Int., 61(3):1124-1135 (2002).
Ye et al., Longitudinal Tracking of Recipient Macrophages in a Rat Chronic Cardiac Allograft Rejection Model with Noninvasive Magnetic Resonance Imaging Using Micrometer-Sized Paramagnetic Iron Oxide Particles. *Circulation.* 2008;118(2):149-156.
Zamboni et al., "Best practices in cancer nanotechnology: perspective from NCI nanotechnology alliance," Clin. Cancer Res. 2012, 18(12):3229-3241.
Zhang et al., "Development of Nanoparticles for Antimicrobial Drug Delivery," Current Medicinal Chemistry, 17(6):585-594 (2010).
Zhao et al., "Small-molecule-directed nanoparticle assembly towards stimuli-responsive nanocomposites," Nature Materials, 8(12):979-985 (2009).
Castro et al., "Effect of a perfluorocarbon emulsion (Fluosol-DA) on reticuloendothelial system clearance function," *Am J. Hematol.,* 1984. 16(1):15-21.
PCT International Search Report and Written Opinion in corresponding PCT Application No. PCT/US16/18446, dated May 3, 2016, pp. 1-12.

* cited by examiner

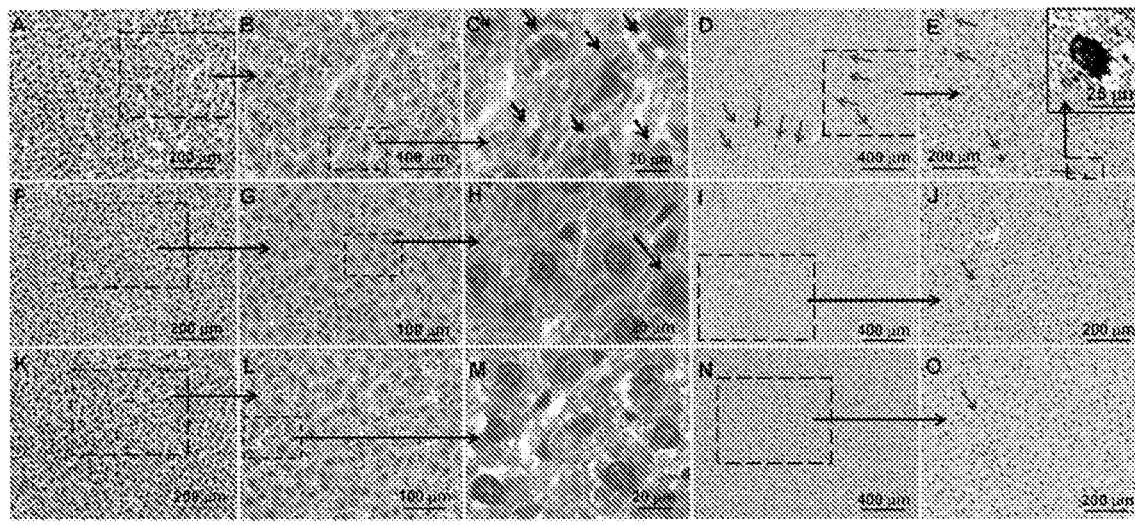
FIGs. 1A-1O
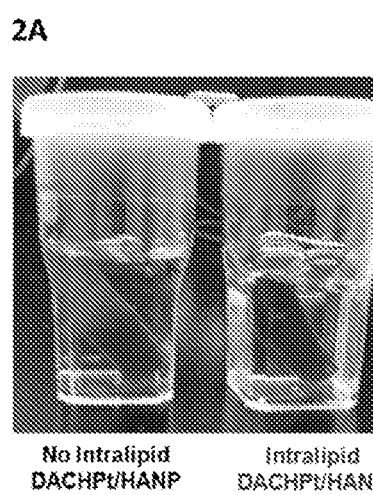
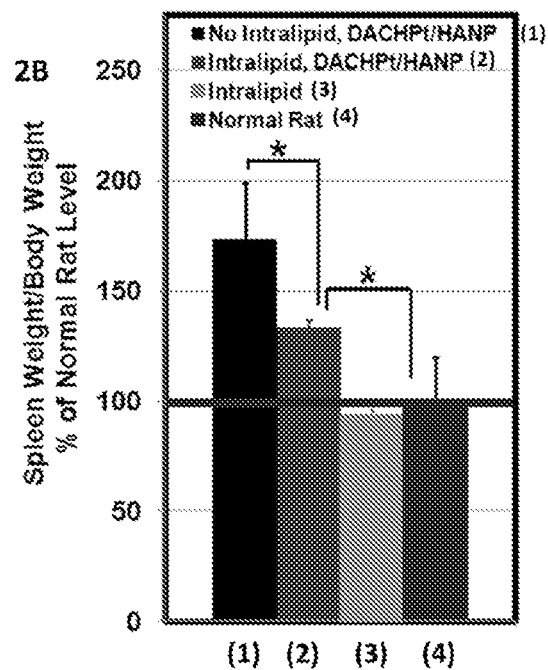
FIGs. 2A-2B

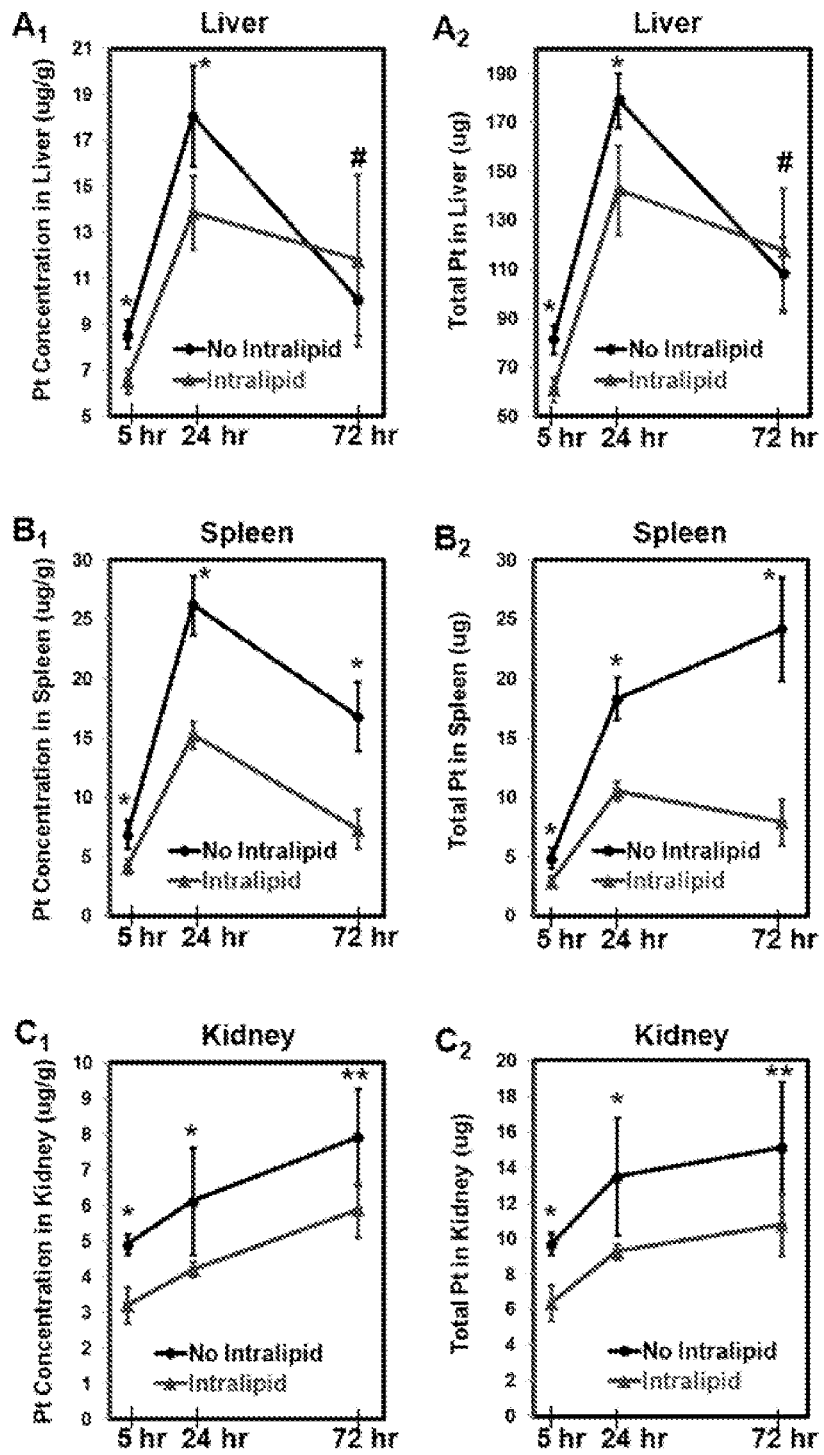
FIGs. 6A₁-6C₂

METHODS TO REDUCE TOXICITIES AND TO IMPROVE BIOAVAILABILITIES OF NANODRUGS

CROSS-REFERENCE TO RELATED APPLICATIONS

This application is a § 371 National Stage Application of PCT/US2016/018446, filed Feb. 18, 2016, which, in turn, claims priority to U.S. Application Ser. No. 62/176,481, filed Feb. 19, 2015, the disclosure of each of which is incorporated by reference herein in its entirety.

STATEMENT REGARDING FEDERALLY SPONSORED RESEARCH OR DEVELOPMENT

This invention was made with government support under the National Institutes of Health under Grant No. P41EB-001977. The government has certain rights in this invention.

TECHNICAL FIELD

This invention generally relates to methods for reducing clearance of nanotherapeutic agents from a subject, and more particularly to pre-administering a nutrition supplement to the subject to reduce clearance of nanotherapeutic agents administered to the subject.

BACKGROUND

This application relates to methods of improving nanotherapeutics. Nanoformulation of platinum (Pt) drugs has the potential to improve the delivery to tumors and reduce toxic side effects. A major challenge for translating nanotherapeutic agents to clinical settings, however, is their rapid clearance by the reticuloendothelial system (RES), hence increasing toxicities on off-target organs and reducing efficacy. In order to significantly improve the therapeutic effects of current drugs, two problems need to be resolved urgently: (i) to improve delivery of the drug specifically to tumors and (ii) to reduce the toxic side effects of the drug. Described herein are methods to increase the bioavailability of nanoformulated anti-cancer chemotherapeutics, and nanotherapeutic agents generally, while decreasing their toxicity in the liver, spleen, and kidney, as well as nutrition supplements for use in the treatment of a disease in a subject, wherein the treatment comprises (i) administering the nutrition supplement; and (ii) administering a nanotherapeutic agent to the subject, wherein said nutrition supplement is administered to the mammal about 0.1 hours to about 24 hours before the nanotherapeutic agent is administered to the subject. Kits comprising the nutrition supplement and nanotherapeutic agent are also provided. Additional

SUMMARY

The present application provides, inter alia, a nutrition supplement for use in the treatment of a disease in a subject, wherein the treatment comprises (i) administering the nutrition supplement; and (ii) administering a nanotherapeutic agent to the subject, wherein said nutrition supplement is administered to the mammal about 0.1 hours to about 24 hours before the nanotherapeutic agent is administered to the subject.

The present application further provides a nutrition supplement for use in the treatment of a cancerous disease in a subject, wherein the treatment comprises (i) administering the nutrition supplement; and (ii) administering a nanotherapeutic agent to the subject, wherein said nutrition supplement is administered to the mammal about 0.1 hours to about 24 hours before the nanotherapeutic agent is administered to the subject.

The present application further provides a nutrition supplement for use in reducing clearance of a nanotherapeutic agent from a subject in the treatment of a disease (e.g., a cancerous disease), wherein the treatment comprises (i) administering the nutrition supplement; and (ii) administering a nanotherapeutic agent to the subject, wherein said nutrition supplement is administered to the mammal about 0.1 hours to about 24 hours before the nanotherapeutic agent is administered to the subject.

In some embodiments, the nutrition supplement for use in reducing clearance of a nanotherapeutic agent from a subject comprises reducing reticuloendothelial system (RES) clearance of the nanotherapeutic agent from the subject.

The present application further provides a nutrition supplement for use in improving the bioavailability of a nanotherapeutic agent in a subject in the treatment of a disease (e.g., a cancerous disease), wherein the treatment comprises (i) administering a nutrition supplement to the subject and (ii) administering the nanotherapeutic agent to the subject, wherein the nutrition supplement is administered between about 0.1 hours and about 24 hours before the nanotherapeutic agent is administered to the subject. In some embodiments, the nutrition supplement for use in improving the bioavailability of a nanotherapeutic agent in a subject comprises improving the bioavailability of the nanotherapeutic agent by about 5% to about 30%, compared to the bioavailability of the nanotherapeutic agent in a corresponding subject without pre-administration of the nutrition supplement. In some embodiments, the nutrition supplement for use in improving the bioavailability of a nanotherapeutic agent in a subject comprises improving the bioavailability of the nanotherapeutic agent by about 5% to about 20%, compared to the bioavailability of the nanotherapeutic agent in a corresponding subject without pre-administration of the nutrition supplement.

The present application further provides a nutrition supplement for use in reducing toxicity of a nanotherapeutic agent in a subject in the treatment of a disease (e.g., a cancerous disease), wherein the treatment comprises (i) administering a nutrition supplement to the subject and (ii) administering the nanotherapeutic agent to the subject, wherein the nutrition supplement is administered between about 0.1 hours and about 24 hours before the nanotherapeutic agent is administered to the subject.

In some embodiments, the nutrition supplement for use in reducing toxicity of a nanotherapeutic agent in a subject comprises reducing liver toxicity of the nanotherapeutic agent in the subject. In some embodiments, the use in reducing liver toxicity comprises decreasing accumulation of the nanotherapeutic agent in the liver. In some embodiments, the accumulation of the nanotherapeutic agent is decreased by about 10% to about 30% in the liver, compared to accumulation of the nanotherapeutic agent in the liver of a corresponding subject without pre-administration of the nutrition supplement. In some embodiments, the accumulation of the nanotherapeutic agent is decreased by about 15% to about 25% in the liver, compared to accumulation of the nanotherapeutic agent in the liver of a corresponding subject without pre-administration of the nutrition supplement.

In some embodiments, the nutrition supplement for use in reducing toxicity of a nanotherapeutic agent in a subject comprises reducing spleen toxicity of the nanotherapeutic agent in the subject. In some embodiments, the use in reducing spleen toxicity comprises decreasing accumulation of the nanotherapeutic agent in the spleen. In some embodiments, the accumulation of the nanotherapeutic agent is decreased by about 25% to about 50% in the spleen, compared to accumulation of the nanotherapeutic agent in the spleen of a corresponding subject without pre-administration of the nutrition supplement. In some embodiments, the accumulation of the nanotherapeutic agent is decreased by about 35% to about 45% in the spleen, compared to accumulation of the nanotherapeutic agent in the spleen of a corresponding subject without pre-administration of the nutrition supplement.

In some embodiments, the nutrition supplement for use in reducing toxicity of a nanotherapeutic agent in a subject comprises reducing kidney toxicity of the nanotherapeutic agent in the subject. In some embodiments, the use in reducing kidney toxicity comprises decreasing accumulation of the nanotherapeutic agent in the kidney. In some embodiments, the accumulation of the nanotherapeutic agent is decreased by about 5% to about 15% in the kidney, compared to accumulation of the nanotherapeutic agent in the kidney of a corresponding subject without pre-administration of the nutrition supplement. In some embodiments, the accumulation of the nanotherapeutic agent is decreased by about 6% to about 12% in the kidney, compared to accumulation of the nanotherapeutic agent in the kidney of a corresponding subject without pre-administration of the nutrition supplement.

In some embodiments, the nutrition supplement is administered between about 0.3 and about 4 hours before the nanotherapeutic agent is administered. In some embodiments, the nutrition supplement is administered between about 0.3 and about 3 hours before the nanotherapeutic agent is administered. In some embodiments, the nutrition supplement is administered between about 0.5 and about 1.5 hours before the nanotherapeutic agent is administered. In some embodiments, the nutrition supplement is administered between about 4 and about 10 hours before the nanotherapeutic agent is administered. In some embodiments, the nutrition supplement is administered between about 10 and about 24 hours before the nanotherapeutic agent is administered. In some embodiments, the nutrition supplement is administered between about 10 and about 15 hours before the nanotherapeutic agent is administered. In some embodiments, the nutrition supplement is administered about 1 hour before the nanotherapeutic agent is administered.

In some embodiments, the nutrition supplement and the nanotherapeutic agent are administered to the subject in separate dosage forms. In some embodiments, the nutrition supplement is administered intravenously to the subject.

In some embodiments, the nanotherapeutic agent comprises a therapeutic agent and a nanocarrier. In some embodiments, the nanotherapeutic agent comprises a therapeutic agent and a nanocarrier, wherein the nanocarrier is selected from the group consisting of a liposome, a lipid-coated nanoparticle, a protein-coated nanoparticle, and a polymer-coated nanoparticle. In some embodiments, the nanotherapeutic agent comprises a therapeutic agent and a hyaluronic acid polymer coating.

In some embodiments, the nanotherapeutic agent comprises a therapeutic agent selected from the group consisting of a chemotherapeutic agent, an anti-inflammatory agent, a steroid, an anti-fungal drug, an anesthetic, and an immunosuppressant. In some embodiments, the nanotherapeutic agent comprises a chemotherapeutic agent. In some embodiments, the chemotherapeutic agent is a platinum-containing chemotherapeutic agent. In some embodiments, the chemotherapeutic agent is a platinum-containing chemotherapeutic agent selected from the group consisting of cisplatin, carboplatin, oxaliplatin, and dichloro(1,2-diaminocyclohexane) platinum(II) (DACHPt). In some embodiments, the chemotherapeutic agent is oxaliplatin or dichloro(1,2-diaminocyclohexane)platinum(II) (DACHPt). In some embodiments, the chemotherapeutic agent is dichloro(1,2-diaminocyclohexane)platinum(II) (DACHPt).

In some embodiments, the nanotherapeutic agent comprises a chemotherapeutic agent and a polymer coated nanoparticle. In some embodiments, the nanotherapeutic agent comprises a chemotherapeutic agent and a hyaluronic acid polymer coated nanoparticle. In some embodiments, the nanotherapeutic agent comprises a platinum-containing chemotherapeutic agent and a hyaluronic acid polymer coated nanoparticle. In some embodiments, the nanotherapeutic agent comprises oxaliplatin or dichloro(1,2-diaminocyclohexane) platinum(II) (DACHPt) and a hyaluronic acid polymer coated nanoparticle. In some embodiments, the nanotherapeutic agent comprises dichloro(1,2-diaminocyclohexane) platinum(II) (DACHPt) and a hyaluronic acid polymer coated nanoparticle.

In some embodiments, the nutrition supplement comprises one or more of soybean oil, vegetable oil, fish oil, phospholipids, and glycerol, or of any combination thereof. In some embodiments, the nutrition supplement is selected from the group consisting of Intralipid® 10%, Intralipid® 20%, and Intralipid® 30%, or any combination thereof. In some embodiments, the nutrition supplement is Intralipid® 20%.

In some embodiments:
the nutrition supplement is selected from the group consisting of Intralipid® 10%, Intralipid® 20%, and Intralipid® 30%, or any combination thereof;
the nanotherapeutic agent comprises a chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises a chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises a platinum-containing chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises oxaliplatin or dichloro(1,2-diaminocyclohexane)platinum(II) (DACHPt) and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises dichloro(1,2-diaminocyclohexane)platinum(II) (DACHPt) and a hyaluronic acid polymer coated nanoparticle; and the nutrition supplement is administered about 1 hour before the nanotherapeutic agent is administered.

In some embodiments, the disease is selected from the group consisting of an autoimmune disease, an inflammatory disease, a fungal infection, or a cancer (i.e., a cancerous disease).

In some embodiments, the cancer is selected from the group consisting of breast cancer, prostate cancer, esophageal cancer, liver cancer, colon cancer, testicular cancer, endometrial cancer, brain cancer, bladder cancer, cancer of the uterus, cancer of the ovary, cervical cancer, lung cancer, sarcoma, bone cancer, pancreatic cancer, renal cancer, stomach cancer, and cancer of the head and neck. In some embodiments, the subject is not concurrently being treated with a parenteral nutrition supplement prior to the administration of step i).

In some embodiments, the nutrition supplement is administered to the subject at a dose of from about 1 g/kg to about 3 g/kg. In some embodiments, the nutrition supplement is administered to the subject at a dose of about 2 g/kg. In some embodiments, a reduced dosage of the nutrition supplement is administered to the subject compared to the dosage administered to a corresponding subject as a parenteral nutrition supplement. In some embodiments, the reduced dosage is less than about 2 g/kg of the nutrition supplement.

In some embodiments, a reduced dosage of the nanotherapeutic agent is administered to the subject compared to the dosage administered to a corresponding subject without pre-administration of the nutrition supplement. In some embodiments, the reduced dosage comprises a sub-therapeutic amount of the nanotherapeutic agent.

In some embodiments, an increased dosage of the nanotherapeutic agent is administered to the subject compared to the dosage administered to a corresponding subject without pre-administration of the nutrition supplement. In some embodiments, the increased dosage comprises a supra-therapeutic amount of the nanotherapeutic agent.

The present application further provides a nutrition supplement for use in reducing reticuloendothelial system (RES) clearance of a nanotherapeutic agent from a subject in the treatment of a disease, wherein the treatment comprises (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered; and the nanotherapeutic agent is a dichloro(1,2-diaminocyclohexane)platinum(II)/hyaluronic acid polymer (DACHPt/HANP) coated nanotherapeutic agent.

The present application further provides a nutrition supplement for use in improving the bioavailability of a nanotherapeutic agent in a subject in the treatment of a disease, wherein the treatment comprises (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered; and the nanotherapeutic agent is a dichloro(1,2-diaminocyclohexane)platinum(II)/hyaluronic acid polymer (DACHPt/HANP) coated nanotherapeutic agent.

The present application further provides a nutrition supplement for use in reducing liver toxicity, spleen toxicity, and kidney toxicity of a nanotherapeutic agent in a subject in the treatment of a disease, wherein the treatment comprises (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered;

the nanotherapeutic agent is a dichloro(1,2-diaminocyclohexane)platinum(II)/hyaluronic acid polymer (DACHPt/HANP) coated nanotherapeutic agent.

The present application further provides a method of reducing clearance of a nanotherapeutic agent from a subject in the treatment of a disease, the method comprising (i) administering a nutrition supplement to the subject and (ii) administering the nanotherapeutic agent to the subject, wherein the nutrition supplement is administered between about 0.1 hours and about 24 hours before the nanotherapeutic agent, is administered to the subject. In some embodiments, the method is a method of reducing reticuloendothelial system (RES) clearance of the nanotherapeutic agent from the subject.

The present application further provides a method of improving the bioavailability of a nanotherapeutic agent in a subject in the treatment of a disease, the method comprising (i) administering a nutrition supplement to the subject and (ii) administering the nanotherapeutic agent to the subject, wherein the nutrition supplement is administered between about 0.1 hours and about 24 hours before the nanotherapeutic agent is administered to the subject.

In some embodiments, the method comprises improving the bioavailability of the nanotherapeutic agent by about 5% to about 30%, compared to the bioavailability of the nanotherapeutic agent in a corresponding subject without pre-administration of the nutrition supplement. In some embodiments, the method comprises improving the bioavailability of the nanotherapeutic agent by about 5% to about 20%, compared to the bioavailability of the nanotherapeutic agent in a corresponding subject without pre-administration of the nutrition supplement.

The present application further provides a method of reducing toxicity of a nanotherapeutic agent in a subject in the treatment of a disease, the method comprising (i) administering a nutrition supplement to the subject and (ii) administering the nanotherapeutic agent to the subject, wherein the nutrition supplement is administered between about 0.1 hours and about 24 hours before the nanotherapeutic agent is administered to the subject. In some embodiments, the method comprises reducing liver toxicity of the nanotherapeutic agent in the subject. In some embodiments, the method of reducing liver toxicity comprises decreasing accumulation of the nanotherapeutic agent in the liver. In some embodiments, the accumulation of the nanotherapeutic agent is decreased by about 10% to about 30% in the liver, compared to accumulation of the nanotherapeutic agent in the liver of a corresponding subject without pre-administration of the nutrition supplement. In some embodiments, the accumulation of the nanotherapeutic agent is decreased by about 15% to about 25% in the liver, compared to accumulation of the nanotherapeutic agent in the liver of a corresponding subject without pre-administration of the nutrition supplement.

In some embodiments, the method comprises reducing spleen toxicity of the nanotherapeutic agent in the subject. In some embodiments, the method of reducing spleen toxicity comprises decreasing accumulation of the nanotherapeutic agent in the spleen. In some embodiments, the accumulation of the nanotherapeutic agent is decreased by about 25% to about 50% in the spleen, compared to accumulation of the nanotherapeutic agent in the spleen of a corresponding subject without pre-administration of the nutrition supplement. In some embodiments, the accumulation of the nanotherapeutic agent is decreased by about 35% to about 45% in the spleen, compared to accumulation of the nanotherapeutic agent in the spleen of a corresponding subject without pre-administration of the nutrition supplement.

In some embodiments, the method comprises reducing kidney toxicity of the nanotherapeutic agent in the subject. In some embodiments, the method of reducing kidney toxicity comprises decreasing accumulation of the nanotherapeutic agent in the kidney. In some embodiments, the accumulation of the nanotherapeutic agent is decreased by about 5% to about 15% in the kidney, compared to accumulation of the nanotherapeutic agent in the kidney of a corresponding subject without pre-administration of the nutrition supplement. In some embodiments, the accumulation of the nanotherapeutic agent is decreased by about 6% to about 12% in the kidney, compared to accumulation of the nanotherapeutic agent in the kidney of a corresponding subject without pre-administration of the nutrition supplement.

In some embodiments, the nutrition supplement is administered between about 0.3 and about 4 hours before the nanotherapeutic agent is administered. In some embodiments, the nutrition supplement is administered between about 0.3 and about 3 hours before the nanotherapeutic agent is administered. In some embodiments, the nutrition supplement is administered between about 0.5 and about 1.5 hours before the nanotherapeutic agent is administered. In some embodiments, the nutrition supplement is administered between about 4 and about 10 hours before the nanotherapeutic agent is administered. In some embodiments, the nutrition supplement is administered between about 10 and about 24 hours before the nanotherapeutic agent is administered. In some embodiments, the nutrition supplement is administered between about 10 and about 15 hours before the nanotherapeutic agent is administered. In some embodiments, the nutrition supplement is administered about 1 hour before the nanotherapeutic agent is administered. In some embodiments, the nutrition supplement and the nanotherapeutic agent are administered to the subject in separate dosage forms. In some embodiments, the nutrition supplement is administered intravenously to the subject.

In some embodiments, the nanotherapeutic agent comprises a therapeutic agent and a nanocarrier. In some embodiments, the nanotherapeutic agent comprises a therapeutic agent and a nanocarrier, wherein the nanocarrier is selected from the group consisting of a liposome, a lipid-coated nanoparticle, a protein-coated nanoparticle, and a polymer-coated nanoparticle.

In some embodiments, the nanotherapeutic agent comprises a therapeutic agent and a hyaluronic acid polymer coating. In some embodiments, the nanotherapeutic agent comprises a therapeutic agent selected from the group consisting of a chemotherapeutic agent, an anti-inflammatory agent, a steroid, an anti-fungal drug, an anesthetic, and an immunosuppressant. In some embodiments, the nanotherapeutic agent comprises a chemotherapeutic agent. In some embodiments, the chemotherapeutic agent is a platinum-containing chemotherapeutic agent. In some embodiments, the chemotherapeutic agent is a platinum-containing chemotherapeutic agent selected from the group consisting of cisplatin, carboplatin, oxaliplatin, and dichloro(1,2-diaminocyclohexane)platinum(II) (DACHPt). In some embodiments, the chemotherapeutic agent is oxaliplatin or dichloro(1,2-diaminocyclohexane)platinum(II) (DACHPt). In some embodiments, the chemotherapeutic agent is dichloro(1,2-diaminocyclohexane)platinum(II) (DACHPt).

In some embodiments, the nanotherapeutic agent comprises a chemotherapeutic agent and a polymer coated nanoparticle. In some embodiments, the nanotherapeutic agent comprises a chemotherapeutic agent and a hyaluronic acid polymer coated nanoparticle. In some embodiments, the nanotherapeutic agent comprises a platinum-containing chemotherapeutic agent and a hyaluronic acid polymer coated nanoparticle. In some embodiments, the nanotherapeutic agent comprises oxaliplatin or dichloro(1,2-diaminocyclohexane) platinum(II) (DACHPt) and a hyaluronic acid polymer coated nanoparticle. In some embodiments, the nanotherapeutic agent comprises dichloro(1,2-diaminocyclohexane) platinum(II) (DACHPt) and a hyaluronic acid polymer coated nanoparticle.

In some embodiments, the nutrition supplement comprises one or more of soybean oil, vegetable oil, fish oil, phospholipids, and glycerol, or of any combination thereof. In some embodiments, the nutrition supplement is selected from the group consisting of Intralipid® 10%, Intralipid® 20%, and Intralipid® 30%, or any combination thereof. In some embodiments, the nutrition supplement is Intralipid® 20%.

In some embodiments:
the nutrition supplement is selected from the group consisting of Intralipid® 10%, Intralipid® 20%, and Intralipid® 30%, or any combination thereof;
the nanotherapeutic agent comprises a chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises a chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises a platinum-containing chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises oxaliplatin or dichloro(1,2-diaminocyclohexane)platinum(II) (DACHPt) and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises dichloro(1,2-diaminocyclohexane)platinum(II) (DACHPt) and a hyaluronic acid polymer coated nanoparticle; and
the nutrition supplement is administered about 1 hour before the nanotherapeutic agent is administered.

In some embodiments, the disease is selected from the group consisting of an autoimmune disease, an inflammatory disease, a fungal infection, or a cancer. In some embodiments, the cancer is selected from the group consisting of breast cancer, prostate cancer, esophageal cancer, liver cancer, colon cancer, testicular cancer, endometrial cancer, brain cancer, bladder cancer, cancer of the uterus, cancer of the ovary, cervical cancer, lung cancer, sarcoma, bone cancer, pancreatic cancer, renal cancer, stomach cancer, and cancer of the head and neck.

In some embodiments, the subject is not concurrently being treated with a parenteral nutrition supplement prior to the administration of step i). In some embodiments, the nutrition supplement is administered to the subject at a dose of from about 1 g/kg to about 3 g/kg. In some embodiments, the nutrition supplement is administered to the subject at a dose of about 2 g/kg.

In some embodiments, a reduced dosage of the nutrition supplement is administered to the subject compared to the dosage administered to a corresponding subject as a parenteral nutrition supplement. In some embodiments, the reduced dosage is less than about 2 g/kg of the nutrition supplement. In some embodiments, a reduced dosage of the nanotherapeutic agent is administered to the subject compared to the dosage administered to a corresponding subject without pre-administration of the nutrition supplement. In some embodiments, the reduced dosage comprises a sub-therapeutic amount of the nanotherapeutic agent.

In some embodiments, an increased dosage of the nanotherapeutic agent is administered to the subject compared to the dosage administered to a corresponding subject without pre-administration of the nutrition supplement. In some embodiments, the increased dosage comprises a supra-therapeutic amount of the nanotherapeutic agent.

The present application further provides a method of reducing reticuloendothelial system (RES) clearance of a nanotherapeutic agent from a subject in the treatment of a disease, the method comprising (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered; and the nanotherapeutic agent is a dichloro(1,2-diaminocyclohexane)platinum(II)/hyaluronic acid polymer (DACHPt/HANP) coated nanotherapeutic agent.

The present application further provides a method of improving the bioavailability of a nanotherapeutic agent in a subject in the treatment of a disease, the method comprising (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered; and the nanotherapeutic agent is a dichloro(1,2-diaminocyclohexane)platinum(II)/hyaluronic acid polymer (DACHPt/HANP) coated nanotherapeutic agent.

The present application further provides a method of reducing liver toxicity, spleen toxicity, and kidney toxicity of a nanotherapeutic agent in a subject in the treatment of a disease, the method comprising (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered;

the nanotherapeutic agent is a dichloro(1,2-diaminocyclohexane)platinum(II)/hyaluronic acid polymer (DACHPt/HANP) coated nanotherapeutic agent.

The present application further provides a kit for use in the treatment of a disease in a subject, said kit comprising a nutrition supplement and a nanotherapeutic agent, wherein said nutrition supplement is to be administered to the mammal from about 0.1 hours to about 24 hours before the nanotherapeutic agent is to be administered to the mammal.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIGS. 1A-1O show that Intralipid® 20% (clinical dose, 2 g/kg) reduces toxic side effects in liver caused by the anti-cancer nanotherapeutic agent, dichloro(1,2-diaminocyclohexane)platinum(II) and a hyaluronic acid polymer coated nanoparticle (DACHPt/HANP). Light microscopy images of hematoxylin/eosin (i.e., H & E) stained are shown in FIGS. 1A-1C, 1F-1H, and 1K-1M) and TUNEL stained liver tissue are shown in FIGS. 1D-1E, 1I-1J, and 1N-1O. FIGS. 1A-1E are from the liver tissues of DACHPt/HANP administrated, but no Intralipid® treated, animals; FIGS. 1F-1J are from the liver tissues of Intralipid® pre-treated animals; FIGS. 1K-1O are from the liver tissues of naïve animals. FIG. 1C is an example of enlarged view of FIG. 1B, which is enlarged from part of FIG. 1A. FIG. 1H is an example of enlarged view of FIG. 1G, which is enlarged from part of FIG. 1F. FIG. 1M is an example of enlarged view of FIG. 1L, which is enlarged from part of FIG. 1K. FIG. 1E is an example of enlarged view of FIG. 1D. FIG. 1J is an example of enlarged view of FIG. 1I. FIG. 1O is an example of enlarged view of FIG. 1N. Black arrows on FIGS. 1C and 1H indicate cell necrosis; red arrows on FIGS. 1D and 1E indicate cell apoptosis.

FIGS. 2A-2B show that Intralipid® 20% (clinical dose, 2 g/kg) pre-treatment can reduce spleen swelling significantly: FIG. 2A depicts a picture of the spleens from DACHPt/HANP treated, without or with Intralipid® treated, SD rats; and FIG. 2B depicts the changes in spleen weight/body weight ratio upon Intralipid® treatment. The ratio from a normal SD rat is treated as 100% (see FIG. 2B, bar (4)). *$p<0.05$.

FIGS. 3A-3E are from the spleen tissues of for which DACHPt/HANP was administered but no Intralipid® treated, animals; FIGS. 3F-3J are from Intralipid® pre-treated animals; FIGS. 3K-3O are from naïve healthy animals. Black arrows on FIG. 3A indicate concurrent abnormal proliferation of mononuclear cells; black arrows on FIGS. 3B, 3C, 3G, and 3H indicate cell necrosis; red arrows on FIGS. 3D and 3E indicate cell apoptosis.

FIGS. 4A-4D are from the kidney tissues of for which DACHPt/HANP was administered, but no Intralipid® treated, animals; FIGS. 4E-4H are Intralipid® pre-treated animals; FIGS. 4I-4L are from naïve healthy animals. Red arrows on FIGS. 4D and 4H indicate cell apoptosis.

FIGS. $6A_1$-$6C_2$ show the changes in concentrations ($6A_1$, $6B_1$, $6C_1$) and total amounts ($6A_2$, $6B_2$, $6C_2$) of Pt in liver ($6A_1$, $6A_2$), spleen ($6B_1$, $6B_2$), and kidney ($6C_1$, $6C_2$) upon Intralipid® 20% (clinical dose, 2 g/kg) pre-treatment, at 5-, 24-, and 72-hr post the DACHPt/HANP administration. P values represent the significance differences from the concentration or amount of Pt in the tissue from the Intralipid® pre-treated group at the same time point. *$p<0.001$; **$p<0.01$; #$p>0.1$.

Figure 7:
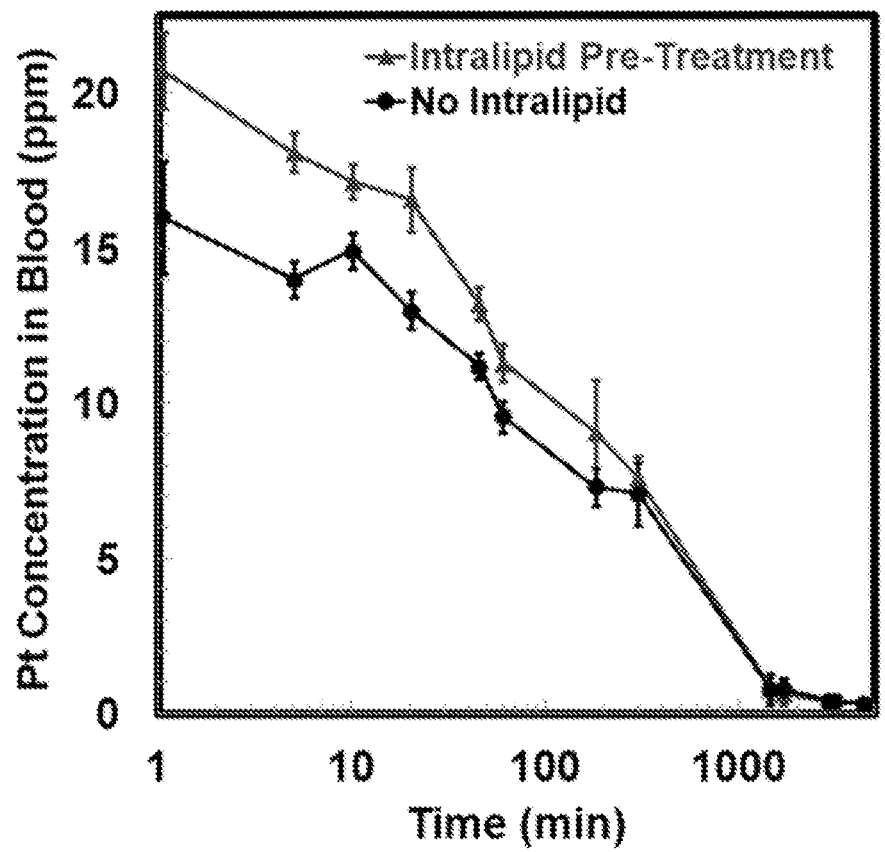

FIG. 7 shows the changes in the Pt concentrations in blood upon Intralipid® 20% (clinical dose, 2 g/kg) pre-treatment during 72 hr. The X-axis represents the duration post DACHPt/HANP injection, in logarithmic scale (base: 10).

Figures 8A, 8B, 8C:
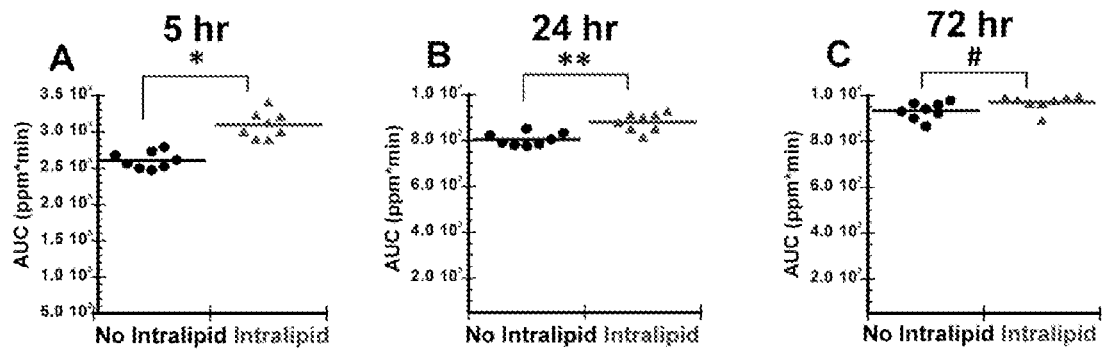

FIGS. 8A-8C show the changes in the bioavailability of DACHPt/HANP nanotherapeutic agent (calculated by the area under the curve (AUC), by the trapezoidal rule, using KaleidaGraph 4.1 (Synergy Software, Reading, Pa.)) upon Intralipid® pre-treatment: (FIG. 8A) 5 hr; (FIG. 8B) 24 hr; (FIG. 8C) 72 hr after the nanotherapeutic agent administration. *$p<0.0001$; **$p<0.001$; #$p>0.05$.

DETAILED DESCRIPTION

Nanomedicine, particularly nanotechnology-based chemotherapeutics, has the potential to improve drug delivery and may generate new preventative, diagnostic, and therapeutic approaches to cancer in areas where improvements may not be obtained using existing technologies. In general, nanocarriers accumulate in solid tumors as a result of the enhanced permeability and retention (EPR) of macromolecules, thereby enhancing their anti-tumor or tumor-diagnosis activity (see e.g., Heger et al, *Nat. Med.,* 2013, 19, 120; Chow et al, *Sci. Transl. Med.* 2013, 5, 216rv214; Chauhan et al, *Nat. Mater.* 2013, 12, 958-962; Wang et al, *Annu. Rev. Med.* 2012, 63, 185-198; Zamboni et al, *Clin. Cancer Res.* 2012, 18, 3229-3241; and Cabral et al, *Proc. Natl. Acad. Sci. USA,* 2013, 110, 11397-11402). Several nanocarrier-based chemotherapeutics, such as Abraxane® and Doxil®, have been approved for treatment of several types of cancer. Studies have shown that the therapeutic performance of oxaliplatin, which is a third generation Pt drug, can be improved by incorporating the central dichloro-(1, 2-diaminocyclohexane)platinum(II) (DACHPt) motif into the core of these types of nanocarriers (see e.g., Cabral et al, *J. Control Release,* 2005, 101, 223-232; Murakami et al, *Sci. Trans. Med.* 2011, 3, 64ra62; Oberoi et al, *Chemother. Res. Pract.* 2012, 905796; and Wu et al, *J. Control Release,* 2014, 189, 1-10).

Currently approved anti-cancer nanotherapeutic agents, namely Abraxane®, Doxil®, DaunoXome®, and DepoCyt®, work by loading traditional cancer chemotherapeutics into nanocarriers. These chemotherapeutics are believed to inhibit mitosis (paclitaxel loaded in Abraxane®), cause DNA intercalation (doxorubicin and daunorubicin loaded in Doxil® and DaunoXome®), and interfere with DNA synthesis (cytarabine loaded in DepoCyt®). Thus, the accumulation of these drugs in mononuclear phagocytic cells in the liver and spleen would cause toxic side effects. For many nanotherapeutic agents, the toxicity in the mononuclear phagocyte system marks an end for further development activities.

A major limitation for both approved and in-development nanotherapeutic agents is their rapid clearance by the cells of the RES/mononuclear phagocyte system (MPS), in particular liver and spleen, which can increase their toxicity to these off-target organs and reduce their efficacy (see e.g., Chow et al, *Sci. Trans. Med.* 2013, 5, 216rv214; Zamboni et al, *Clin. Cancer Res.* 2012, 18, 3229-3241; and Albanese et al, *Annu. Rev. Biomed. Eng.* 2012, 14, 1-16). Strategies that decrease RES uptake and/or increase the bioavailability of nanomedicines can improve tumor targeting and decrease the side effects. Many studies have been conducted to decrease RES clearance and to increase the tumor targeting of nanomedicines by modifying nanoparticle characteristics, such as the size, shape, charge, surface property, and composition (see e.g., Neuberger et al, *Journal of Magnatism and Magnetic Materials,* 2005, 293, 483-496; Arvizo et al, *PLoS One,* 2011, 6, e24374; Maesaki et al, *Curr. Pharm. Des.* 2002, 8, 443-440; Romberg et al, *Pharm. Res.* 2008, 25, 55-71; Jokerst et al, *Nanomedicine (Lond),* 2011, 6, 715-728; and Alexis et al, *Mol. Pharm.* 2008, 5, 505-515. In general, the total accumulation of the anti-cancer nanotherapeutic agents in the tumor represents a small fraction of total injected dose (1-10%). The majority (40-80%) of the injected nanomedicines end up in the liver and spleen (see e.g., Alexis et al.). Moreover, each new modification to the nanotherapeutic agent requires thorough toxicity, pharmacology, and biomechanics studies before translating to a clinical setting.

In addition, the development of targeted nanomedicine has made an impact in new drug development in neurology, cardiology, and inflammation. The EPR effect is found not only in cancer, but also in a range of inflammatory diseases, such as atherosclerosis. Accordingly, the disclosure provided herein for methods of administering nutritional supplements can have applications beyond the treatment of cancerous diseases.

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "therapeutically effective amount" of a composition with respect to the subject method of treatment, refers to an amount of the composition(s) in a preparation which, when administered as part of a desired dosage regimen (to a subject, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting one or more of the symptoms, clinical signs, and underlying pathology of a condition in a manner to improve or stabilize a patient's condition.

Nutrition Supplements

The present application provides, inter alia, a nutrition supplement for use in the methods provided herein. As used herein, the term "nutrition supplement" refers to a composition for providing nutrition to a subject in need thereof, wherein the subject may not be capable of performing the normal processes of eating and digestion. In some embodiments, the nutrition supplement is a parenteral nutrition supplement (i.e., a nutrition supplement to be to the subject via intravenous administration). In some embodiments, the nutrition supplement comprises one or more nutrients selected from the group consisting of carbohydrates (e.g., glucose), amino acids, lipids, vitamins, and dietary minerals. In some embodiments, the nutrition supplement is a total parenteral nutrition (TPN) supplement. In some embodiments, the nutrition supplement is a peripheral parenteral nutrition (PPN) supplement. In some embodiments, the nutrition supplement is a parenteral nutrition supplement approved by the United States Food and Drug Administration. In some embodiments, the nutrition supplement comprises one or more amino acid supplements. In some embodiments, the nutrition supplement comprises one or more of Aminosyn®, AMINOSYN®-HBC, AMINOSYN®-HF, AMINOSYN®-RF, BranchAmin®, FreAmine HBC®, FreAmine® III, HepatAmine®, Kabiven®, Perikabiven®, Novamine®, Premasol, ProcalAmine®, ProSol, RenAmin®, TrophAmine®, or any combination thereof.

In some embodiments, the nutrition supplement comprises a fat emulsion. In some embodiments, the nutrition supplement is a fat emulsion. In some embodiments, the nutrition supplement comprises one or more of soybean oil, vegetable oil, fish oil, phospholipids, and glycerol, or any combination thereof. In some embodiments, the nutrition supplement is selected from the group consisting of Intralipid® 10%, Intralipid® 20%, and Intralipid® 30%, or any combination thereof. In some embodiments, the nutrition supplement is Intralipid® 20%.

In the methods described herein, an amount of nutrition supplement is administered to the subject in an amount effective to reduce clearance of a nanotherapeutic agent from the subject. As used herein, the term "effective amount" refers to an amount (or amounts) of a nutrition supplement that reduces clearance of a nanotherapeutic agent without inducing significant toxicity to the host.

An effective amount of nutrition supplement, the frequency of administration, and duration of administration can be determined by a physician, according to the relevant circumstances, including the condition to be treated, the chosen route of administration, the actual nutrition supplement administered, the age, weight, and response of the individual subject, the severity of the subject's symptoms, and the like.

In some embodiments, a single pre-treatment (e.g., a single intravenous administration) of the nutrition supplement is sufficient to reduce clearance of the nanotherapeutic agent from the subject. In some embodiments, the pre-treatment can comprise multiple administrations of the nutrition supplement at various intervals and over different periods of time as required. In some embodiments, the nutrition supplement is administered multiple times (e.g., two, three, four, or more times), and at least one of the administrations is between about 0.1 hours and about 5 hours before the administration of the nanotherapeutic agent. In some embodiments, multiple administrations of the nutrition supplement are administered between about 0.1 hours and about 24 hours before the administration of the nanotherapeutic agent to the subject. In some embodiments, the methods provided herein are repeated multiple times in the treatment of the subject (e.g., steps (i) and (ii) of the methods provided herein are repeated multiple times.

In some embodiments, the nutrition supplement is administered to the subject at a dose of from about 0.5 g/kg to about 5 g/kg, for example, about 0.5 g/kg to about 5 g/kg, about 0.5 g/kg to about 3 g/kg, about 0.5 g/kg to about 1 g/kg, about 1 g/kg to about 5 g/kg, about 1 g/kg to about 3 g/kg, or about 3 g/kg to about 5 g/kg. In some embodiments, the nutrition supplement is administered to the subject at a dose of from about 1 g/kg to about 3 g/kg. In some embodiments, the nutrition supplement is administered to the subject at a dose of about 2 g/kg. In some embodiments, the nutrition supplement is Intralipid® 20% and is administered to the subject at a dose of from about 1 g/kg to about 3 g/kg. In some embodiments, the nutrition supplement is Intralipid® 20% and is administered to the subject at a dose of about 2 g/kg. In some embodiments, a reduced dosage of the nutrition supplement is administered to the subject compared to the dosage administered to a corresponding subject as a parenteral nutrition supplement. In some embodiments, the reduced dosage is less than about 2 g/kg of the nutrition supplement. In some embodiments, the nutrition supplement is administered to the subject via intravenous administration.

Nanotherapeutic Agents

The present application further provides nanotherapeutic agents for use in the methods provided herein. As used herein, the term "nanotherapeutic agent" is a term known in the art and refers to one or more therapeutic agents formulated for use in nanomedicine (e.g., a therapeutic agent in combination with a nanocarrier).

In some embodiments, the nanotherapeutic agent comprises a therapeutic agent and a nanocarrier. As used herein, the term "nanocarrier" refers to a nanomaterial (e.g., a nanoparticle) that is conjugated to the therapeutic agent (e.g., covalently bonded, ionically bonded, a coating on the therapeutic agent, a nanomaterial that encapsulates the therapeutic agent, and the like). Example nanocarriers include, but are not limited to, liposomes, lipid-coated nanoparticles, protein-coated nanoparticles (e.g., albumin and milk protein casein), and polymer-coated nanoparticles (e.g., chitosan, dextran, carboxymethylated dextran, poly (ecaprolactone), hyaluronic acid (HA) polymer, polyethylene glycol (PEG), poly(lactide) (PLA) and poly(lactide-coglycolide) (PLGA), poly(vinyl pyrrolidone), poly (ethyleneimine), poly(aspartic acid), and N-(2-hydroxypropyl) methacrylamide copolymers). Additional examples of nanocarriers include nanocomplex formed with heparin and protamine (see e.g., Thu et al, *Nat. Med.,* 2012, 18, 463-467). Additional examples may be found, for example, in Bulte et al, *NMR Biomed,* 2004, 17, 484-499, the disclosure of which is incorporated by reference herein in its entirety.

In some embodiments, the surface of a nanocarrier (e.g., a nanoparticle) can comprise one or more reactive functional groups such as thiols, chloromethyl, bromomethyl, hydroxyls, amines, carboxylic acid or activated ester, vinylsulfonyls, aldehydes, epoxies, hydrazides, succinimidyl esters, maleimides, α-halo carbonyl moieties (such as iodoacetyls), isocyanates, isothiocyanates, 4-fluoro-5-nitro-benzoate, and aziridines. For example, the surface of a nanocarrier (e.g., a nanoparticle) can comprise a reactive functional group such as a thiol, a carboxylic acid, an amine, 4-fluoro-5-nitro-benzoate, or a carboxylic acid activated ester. Reactive functional groups may be useful for conjugating (i.e., bonding or attaching) the nanocarrier (e.g., a nanoparticle) to the therapeutic agent.

In some embodiments, the nanotherapeutic agent comprises a therapeutic agent and a nanocarrier, wherein the nanocarrier is selected from the group consisting of a liposome, a lipid-coated nanoparticle, a protein-coated nanoparticle, and a polymer-coated nanoparticle.

In some embodiments, the nanotherapeutic agent comprises a therapeutic agent and a polymer coating. In some embodiments, nanotherapeutic agent comprises a therapeutic agent and a hyaluronic acid polymer coating.

In some embodiments, the nanotherapeutic agent comprises a therapeutic agent selected from the group consisting of a chemotherapeutic agent, an anti-inflammatory agent, a steroid, an anti-fungal drug, an anesthetic, and an immunosuppressant.

Example chemotherapeutic agents include, but are not limited to, proteosome inhibitors (e.g., bortezomib), thalidomide, revlimid, DNA-damaging agents (e.g., melphalan, doxorubicin, cyclophosphamide, vincristine, etoposide, carmustine) cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Smll, triapine, didox, trimidox, amidox, 3-AP, MDL-101,731, bendamustine, ofatumumab, and GS-1101 (also known as CAL-101). Example nanotherapeutic agents comprising chemotherapeutic agents include, but are not limited to, Abraxane®, Marqibo®, Doxil/Caelyx, DepoCyt®, and Onivyde™.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib. One example of a nanotherapeutic agent comprising an anti-inflammatory agent is Visudyne.

Example steroids include, but are not limited to, corticosteroids such as cortisone, dexamethasone, hydrocortisone, methylprednisolone, prednisolone, and prednisone.

Example anti-fungal agents include, but are not limited to, polyene anti-fungal agents (e.g., amphotericin B and candicidin), imidazole anti-fungal agents (e.g., bifonazole, clotrimazole, and econazole), triazole anti-fungal agents (e.g., albaconazole, efinaconazole, and fluconazole), thiazole anti-fungal agents (e.g., abafungin), allylamine anti-fungal agents (e.g., amorolfin, butenafine, and naftifine), echinocandins (e.g., anidulafungin and caspofungin). One example of a nanotherapeutic agent comprising an anti-fungal agent is Amphotericin B (AmB).

Example anesthetics include, but are not limited to local anesthetics (e.g., lidocaine, procain, and ropivacaine), intravenous anesthetics (e.g., amobarbital, methohexital, diazepam, lorazepam, etomidate, ketamine, propofol, alfentanil, and fentanyl). One example of a nanotherapeutic agent comprising an anesthetic agent is DepoDur®.

Example immunosuppressants include, but are not limited to, azathioprine, chlorambucil, cyclophosphamide, cyclosporine, daclizumab, infliximab, methotrexate, and tacrolimus. Example nanotherapeutic agents comprising an immunosuppressant include, but are not limited to, certolizumab pegol and glatiramer acetate.

In some embodiments, the nanotherapeutic agent comprises a chemotherapeutic agent. In some embodiments, the chemotherapeutic agent is a platinum-containing chemotherapeutic agent. Example platinum-containing chemotherapeutic agents include but are not limited to cisplatin, carboplatin, oxaliplatin, and dichloro(1,2-diaminocyclohexane)platinum(II) (DACHPt). In some embodiments, the platinum-containing is selected from the group consisting of cisplatin, carboplatin, oxaliplatin, and dichloro(1,2-diaminocyclohexane)platinum(II) (DACHPt). In some embodiments, the chemotherapeutic agent is oxaliplatin or dichloro(1,2-diaminocyclohexane)platinum(II) (DACHPt). In some embodiments, the chemotherapeutic agent is dichloro(1,2-diaminocyclohexane)platinum(II) (DACHPt).

In some embodiments, the nanotherapeutic agent comprises a chemotherapeutic agent and a polymer coated nanoparticle. In some embodiments, the nanotherapeutic agent comprises a chemotherapeutic agent and a hyaluronic acid polymer coated nanoparticle. In some embodiments, the nanotherapeutic agent comprises a platinum-containing chemotherapeutic agent and a hyaluronic acid polymer coated nanoparticle. In some embodiments, the nanotherapeutic agent comprises oxaliplatin or dichloro(1,2-diaminocyclohexane)platinum(II) (DACHPt) and a hyaluronic acid polymer coated nanoparticle. In some embodiments, the nanotherapeutic agent comprises dichloro(1,2-diaminocyclohexane) latinum(II) (DACHPt) and a hyaluronic acid polymer coated nanoparticle. In some embodiments, the nanotherapeutic agent is a dichloro(1,2-diaminocyclohexane)platinum(II) (DACHPt) hyaluronic acid polymer nanotherapeutic agent.

In some embodiments, a reduced dosage of the nanotherapeutic agent is administered to the subject compared to the dosage administered to a corresponding subject without administration of the nutrition supplement. In some embodiments, a reduced dosage of the nanotherapeutic agent is administered to the subject compared to the dosage administered to a corresponding subject without pre-administration of the nutrition supplement. In some embodiments, the reduced dosage comprises a sub-therapeutic amount of the nanotherapeutic agent. In some embodiments, the sub-therapeutic amount is from about 10% to about 90% of the therapeutic amount of the nanotherapeutic agent, for example about 10% to about 90%, about 10% to about 80%, about 10% to about 70%, about 10% to about 60%, about 10% to about 50%, about 10% to about 40%, about 10% to about 30%, about 10% to about 20%, about 20% to about 90%, about 20% to about 80%, about 20% to about 70%, about 20% to about 60%, about 20% to about 50%, about 20% to about 40%, about 20% to about 30%, about 30% to about 90%, about 30% to about 80%, about 30% to about 70%, about 30% to about 60%, about 30% to about 50%, about 30% to about 40%, about 40% to about 90%, about 40% to about 80%, about 40% to about 70%, about 40% to about 60%, about 40% to about 50%, about 50% to about 90%, about 50% to about 80%, about 50% to about 70%, about 50% to about 60%, about 60% to about 90%, about 60% to about 80%, about 60% to about 70%, about 70% to about 90%, about 70% to about 80%, or about 80% to about 90%.

In some embodiments, an increased dosage of the nanotherapeutic agent is administered to the subject compared to the dosage administered to a corresponding subject without administration of the nutrition supplement. In some embodiments, an increased dosage of the nanotherapeutic agent is administered to the subject compared to the dosage administered to a corresponding subject without pre-administration of the nutrition supplement. In some embodiments, the increased dosage comprises a supra-therapeutic amount of the nanotherapeutic agent. In some embodiments, the supra-therapeutic amount is from about 110% to about 200% of the therapeutic amount of the nanotherapeutic agent, for example about 110% to about 200%, about 110% to about 190%, about 110% to about 180%, about 110% to about 170%, about 110% to about 160%, about 110% to about 150%, about 110% to about 140%, about 110% to about 130%, about 110% to about 120%, about 120% to about 200%, about 120% to about 190%, about 120% to about 180%, about 120% to about 170%, about 120% to about 160%, about 120% to about 150%, about 120% to about 140%, about 120% to about 130%, about 130% to about 200%, about 130% to about 190%, about 130% to about 180%, about 130% to about 170%, about 130% to about 160%, about 130% to about 150%, about 130% to about 140%, about 140% to about 200%, about 140% to about 190%, about 140% to about 180%, about 140% to about 170%, about 140% to about 160%, about 150% to about 200%, about 150% to about 190%, about 150% to about 180%, about 150% to about 170%, about 150% to about 160%, about 160% to about 200%, about 160% to about 190%, about 160% to about 180%, about 160% to about 170%, about 170% to about 200%, about 170% to about 190%, about 170% to about 180%, about 180% to about 200%, about 180% to about 190%, or about 190% to about 200%.

In some embodiments, a single administration (e.g., a single intravenous administration) of the nanotherapeutic agent is sufficient for performing the methods provided herein (e.g., reducing clearance of the nanotherapeutic agent from a subject, increasing bioavailability of a nanotherapeutic agent in a subject, reducing toxicity of a nanotherapeutic agent in a subject, and the like). In some embodiments, multiple administrations of the nanotherapeutic agent at various intervals and over different periods of time may be required. In some embodiments, the nanotherapeutic agent is administered multiple times (e.g., two, three, four, or more times), and at least one of the administrations is between about 0.1 hours and about 24 hours after the administration of the nutrition supplement. In some embodiments, multiple administrations of the nanotherapeutic agent occur between about 0.1 hours and about 24 hours after the administration of the nutrition supplement to the subject. In some embodiments, at least one administration of the nanotherapeutic agent is not preceded by an administration of the nutrition supplement. In some embodiments, only the first administration of the nanotherapeutic agent is preceded by administration of the nutrition supplement. In some embodiments, each administration of the nanotherapeutic agent is preceded by administration of the nanotherapeutic agent.

In some embodiments, the amount of nutrition supplement administered is constant over the course of the treatment regimen (e.g., each administration comprises the about the same dose of the nutrition supplement). In some embodiments, the amount of nutrition supplement administered is increased over the course of the treatment regimen (e.g., a second administration comprises an increased dosage of the nutrition supplement compared to the first administration, and the like). In some embodiments, the amount of nutrition supplement administered is decreased over the course of the treatment regimen (e.g., a second administration comprises a decreased dosage of the nutrition supplement compared to the first administration, and the like).

In some embodiments, the amount of nanotherapeutic agent administered is constant over the course of the treatment regimen (e.g., each administration comprises the about the same dose of the nanotherapeutic agent). In some embodiments, the amount of nanotherapeutic agent administered is increased over the course of the treatment regimen (e.g., a second administration comprises an increased dosage of the nanotherapeutic agent compared to the first administration, and the like). In some embodiments, the amount of nanotherapeutic agent administered is decreased over the course of the treatment regimen (e.g., a second administration comprises a decreased dosage of the nanotherapeutic agent compared to the first administration, and the like).

The nanotherapeutic agent can be effective over a wide dosage range and is generally administered in a pharmaceutically effective amount. It will be understood, however, that the amount of the nanotherapeutic agent actually administered will usually be determined by a physician, according to the relevant circumstances, including the condition to be treated, the chosen route of administration, the actual nanotherapeutic agent administered, the age, weight, and response of the individual subject, the severity of the subject's symptoms, and the like.

Methods of Use

The present application further provides a method of treating a disease in a subject (e.g., an autoimmune disease, an inflammatory disease, a fungal infection, or cancer), wherein the treatment comprises (i) administering the nutrition supplement; and (ii) administering a nanotherapeutic agent to the subject, wherein said nutrition supplement is administered to the mammal about 0.1 hours to about 24 hours before the nanotherapeutic agent is administered to the subject.

The present application further provides a nutrition supplement for use in the treatment of a disease in a subject (e.g., an autoimmune disease, an inflammatory disease, a fungal infection, or a cancerous disease) wherein the treatment comprises (i) administering the nutrition supplement; and (ii) administering a nanotherapeutic agent to the subject, wherein said nutrition supplement is administered to the mammal about 0.1 hours to about 24 hours before the nanotherapeutic agent is administered to the subject.

The present application further provides a method of reducing clearance of a nanotherapeutic agent from a subject in the treatment of a disease. In some embodiments, the method comprises (i) administering a nutrition supplement to the subject and (ii) administering the nanotherapeutic agent to the subject. In some embodiments, the nutrition supplement is administered between about 0.1 hours and about 24 hours before the nanotherapeutic agent is administered to the subject. In some embodiments, the method is a method of reducing RES clearance of the nanotherapeutic agent from the subject.

In some embodiments, the method is a method of reducing RES clearance of the nanotherapeutic agent from the subject by about 5% to about 50% compared to a corresponding subject without pre-administration of the nutrition supplement, for example, about 5% to about 50%, about 5% to about 40%, about 5% to about 30%, about 5% to about 20%, about 5% to about 10%, about 10% to about 50%, about 10% to about 40%, about 10% to about 30%, about 10% to about 20%, about 20% to about 50%, about 20% to about 40%, about 20% to about 30%, about 30% to about 50%, about 30% to about 40%, or about 30% to about 40%.

The present application further provides a method of improving the bioavailability of a nanotherapeutic agent in a subject in the treatment of a disease. In some embodiments, the method comprises (i) administering a nutrition supplement to the subject and (ii) administering the nanotherapeutic agent to the subject. In some embodiments, the nutrition supplement is administered between about 0.1 hours and about 24 hours before the nanotherapeutic agent is administered to the subject.

In some embodiments, the method comprises improving the bioavailability of the nanotherapeutic agent by about 5% to about 50%, compared to the bioavailability of the nanotherapeutic agent in a corresponding subject without pre-administration of the nutrition supplement, for example, by about 5% to about 50%, by about 5% to about 40%, by about 5% to about 30%, by about 5% to about 20%, by about 5% to about 10%, by about 10% to about 50%, by about 10% to about 40%, by about 10% to about 30%, by about 10% to about 20%, by about 20% to about 50%, by about 20% to about 40%, by about 20% to about 30%, by about 30% to about 50%, by about 30% to about 40%, or by about 40% to about 50%.

In some embodiments, the method comprises improving the bioavailability of the nanotherapeutic agent by about 5% to about 30%, compared to the bioavailability of the nanotherapeutic agent in a corresponding subject without pre-administration of the nutrition supplement. In some embodiments, the method comprises improving the bioavailability of the nanotherapeutic agent by about 5% to about 20%, compared to the bioavailability of the nanotherapeutic agent in a corresponding subject without pre-administration of the nutrition supplement.

The present application further provides a method of reducing toxicity of a nanotherapeutic agent in a subject in the treatment of a disease. In some embodiments, the method comprises (i) administering a nutrition supplement to the subject and (ii) administering the nanotherapeutic agent to the subject. In some embodiments, the nutrition supplement is administered between about 0.1 hours and about 24 hours before the nanotherapeutic agent is administered to the subject.

In some embodiments, the method comprises reducing the toxicity of the nanotherapeutic agent in one or more internal organs of the subject. In some embodiments, the method comprises reducing the toxicity of the nanotherapeutic agent in one or more internal organs associated with the RES in the subject.

In some embodiments, the method comprises reducing liver toxicity of the nanotherapeutic agent in the subject. In some embodiments, the method of reducing liver toxicity comprises decreasing accumulation of the nanotherapeutic agent in the liver. Examples of liver toxicity include, but are not limited to, fatal liver toxicity and elevated levels of aspartate aminotransferase and/or ALT.

In some embodiments, the accumulation of the nanotherapeutic agent is decreased by about 5% to about 50% in the liver, compared to accumulation of the nanotherapeutic agent in the liver of a corresponding subject without pre-administration of the nutrition supplement, for example, by about 5% to about 50%, by about 5% to about 40%, by about 5% to about 30%, by about 5% to about 20%, by about 5% to about 10%, by about 10% to about 50%, by about 10% to about 40%, by about 10% to about 30%, by about 10% to about 20%, by about 20% to about 50%, by about 20% to about 40%, by about 20% to about 30%, by about 30% to about 50%, by about 30% to about 40%, or by about 40% to about 50%. In some embodiments, the accumulation of the nanotherapeutic agent is decreased by about 10% to about 30% in the liver, compared to accumulation of the nanotherapeutic agent in the liver of a corresponding subject without pre-administration of the nutrition supplement. In some embodiments, the accumulation of the nanotherapeutic agent is decreased by about 15% to about 25% in the liver, compared to accumulation of the nanotherapeutic agent in the liver of a corresponding subject without pre-administration of the nutrition supplement.

In some embodiments, the method comprises reducing spleen toxicity of the nanotherapeutic agent in the subject. In some embodiments, the method of reducing spleen toxicity comprises decreasing accumulation of the nanotherapeutic agent in the spleen. An example of spleen toxicity includes, but is not limited to, enlarged spleen.

In some embodiments, the accumulation of the nanotherapeutic agent is decreased by about 5% to about 50% in the spleen, compared to accumulation of the nanotherapeutic agent in the spleen of a corresponding subject without pre-administration of the nutrition supplement, for example, by about 5% to about 50%, by about 5% to about 40%, by about 5% to about 30%, by about 5% to about 20%, by about 5% to about 10%, by about 10% to about 50%, by about 10% to about 40%, by about 10% to about 30%, by about 10% to about 20%, by about 20% to about 50%, by about 20% to about 40%, by about 20% to about 30%, by about 30% to about 50%, by about 30% to about 40%, or by about 40% to about 50%. In some embodiments, the accumulation of the nanotherapeutic agent is decreased by about 25% to about 50% in the spleen, compared to accumulation of the nanotherapeutic agent in the spleen of a corresponding subject without pre-administration of the nutrition supplement. In some embodiments, the accumulation of the nanotherapeutic agent is decreased by about 35% to about 45% in the spleen, compared to accumulation of the nanotherapeutic agent in the spleen of a corresponding subject without pre-administration of the nutrition supplement.

In some embodiments, the method comprises reducing kidney toxicity of the nanotherapeutic agent in the subject. In some embodiments, the method of reducing kidney toxicity comprises decreasing accumulation of the nanotherapeutic agent in the kidney. An example of kidney toxicity includes, but is not limited to, nephrotoxicity.

In some embodiments, the accumulation of the nanotherapeutic agent is decreased by about 5% to about 50% in the kidney, compared to accumulation of the nanotherapeutic agent in the kidney of a corresponding subject without pre-administration of the nutrition supplement, for example, by about 5% to about 50%, by about 5% to about 40%, by about 5% to about 30%, by about 5% to about 20%, by about 5% to about 10%, by about 10% to about 50%, by about 10% to about 40%, by about 10% to about 30%, by about 10% to about 20%, by about 20% to about 50%, by about 20% to about 40%, by about 20% to about 30%, by about 30% to about 50%, by about 30% to about 40%, or by about 40% to about 50%. In some embodiments, the accumulation of the nanotherapeutic agent is decreased by about 5% to about 15% in the kidney, compared to accumulation of the nanotherapeutic agent in the kidney of a corresponding subject without pre-administration of the nutrition supplement. In some embodiments, the accumulation of the nanotherapeutic agent is decreased by about 6% to about 12% in the kidney, compared to accumulation of the nanotherapeutic agent in the kidney of a corresponding subject without pre-administration of the nutrition supplement.

In some embodiments, the nutrition supplement is administered between about 0.1 and about 24 hours before the nanotherapeutic agent is administered, for example, between about 0.1 hours and about 24 hours, about 0.1 hours and about 12 hours, about 0.1 hours and about 8 hours, about 0.1 hours and about 4 hours, about 0.1 hours and about 2 hours, about 0.1 hours and about 1 hour, about 0.1 hours and about 0.5 hours, between about 0.5 hours and about 24 hours, about 0.5 hours and about 12 hours, about 0.5 hours and about 8 hours, about 0.5 hours and about 4 hours, about 0.5 hours and about 2 hours, about 0.5 hours and about 1 hour, between about 1 hour and about 24 hours, about 1 hour and about 12 hours, about 1 hour and about 8 hours, about 1 hour and about 4 hours, about 1 hour and about 2 hours, between about 2 hours and about 24 hours, about 2 hours and about 12 hours, about 2 hours and about 8 hours, about 2 hours and about 4 hours, between about 4 hours and about 24 hours, about 4 hours and about 12 hours, about 4 hours and about 8 hours, between about 8 hours and about 24 hours, about 8 hours and about 12 hours, or between about 12 hours and about 24 hours.

In some embodiments, the nutrition supplement is administered between about 0.3 and about 4 hours before the nanotherapeutic agent is administered. In some embodiments, the nutrition supplement is administered between about 0.3 and about 3 hours before the nanotherapeutic agent is administered. In some embodiments, the nutrition supplement is administered between about 0.5 and about 1.5 hours before the nanotherapeutic agent is administered. In some embodiments, the nutrition supplement is administered between about 4 and about 10 hours before the nanotherapeutic agent is administered. In some embodiments, the nutrition supplement is administered between about 10 and about 24 hours before the nanotherapeutic agent is administered. In some embodiments, the nutrition supplement is administered between about 10 and about 15 hours before the nanotherapeutic agent is administered. In some embodiments, the nutrition supplement is administered about 1 hour before the nanotherapeutic agent is administered.

In some embodiments:
the nutrition supplement is selected from the group consisting of Intralipid® 10%, Intralipid® 20%, and Intralipid® 30%, or any combination thereof;
the nanotherapeutic agent comprises a chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises a chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises a platinum-containing chemotherapeutic agent and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises oxaliplatin or dichloro(1,2-diaminocyclohexane) platinum(II) (DACHPt) and a hyaluronic acid polymer coated nanoparticle; and
the nutrition supplement is administered about 1 hour before the nanotherapeutic agent is administered.

In some embodiments:
the nutrition supplement is Intralipid® 20%;
the nanotherapeutic agent comprises dichloro(1,2-diaminocyclohexane) platinum(II) (DACHPt) and a hyaluronic acid polymer coated nanoparticle; and
the nutrition supplement is administered about 1 hour before the nanotherapeutic agent is administered.

In some embodiments, the subject is being treated for a disease selected from the group consisting of an autoimmune disease, an inflammatory disease, a fungal infection, or a cancer. In some embodiments, the methods provided herein are performed in combination with the administration of one or more additional therapeutic agents useful for the treatment of the disease. In some embodiments, the one or more additional therapeutic agents is one or more of the therapeutic agents provided herein.

In some embodiments, the disease is an autoimmune disease. Example autoimmune diseases include, but are not limited to, arthritis (e.g., rheumatoid arthritis, osteoarthritis, psoriatic arthritis), multiple sclerosis (e.g., relapsing-remitting multiple sclerosis), systemic lupus erythematous, asthma, autoimmune pancreatitis, psoriasis, glomerulonephritis, encephalitis, myasthenia gravis, Sjögren's syndrome. In some embodiments, the disease is selected from the group consisting of relapsing-remitting multiple sclerosis, rheumatoid arthritis, and psoriatic arthritis.

In some embodiments, the disease is an inflammatory disease. Example inflammatory diseases include, but are not limited to, inflammatory heart disease (e.g., atherosclerosis), thrombosis, meningitis, benign prostatic hypertrophy, inflammatory bowel disease (e.g., Crohn's disease and ulcerative colitis), and inflammatory eye disease (e.g., macular degeneration). In some embodiments, the inflammatory disease is selected from the group consisting of inflammatory heart diseases, inflammatory bowel disease, and inflammatory eye disease.

In some embodiments, the disease is a fungal infection. Example fungal infections include, but are not limited to, aspergillosis, blastomycosis, candidiasis, cryptococcal meningitis, coccidioidomycosis (Valley Fever), *C. neoformans* infection, *C. gattii* infection, a fungal eye infection, histoplasmosis, mucormycosis, *Pneumocystis* pneumonia (PCP), ringworm, and sporotrichosis.

In some embodiments, the disease is a cancer (i.e., a cancerous disease). Example cancers include, but are not limited to, breast cancer, prostate cancer, esophageal cancer, liver cancer, colon cancer, testicular cancer, endometrial cancer, brain cancer, bladder cancer, cancer of the uterus, cancer of the ovary, cervical cancer, lung cancer, sarcoma, bone cancer, pancreatic cancer, renal cancer, stomach cancer, and cancer of the head and neck. In some embodiments, the cancer is selected from the group consisting of breast cancer, ovarian cancer, pancreatic cancer, lung cancer, blood cancer, and head and neck cancer. In some embodiments, the cancer is selected from the group consisting of In some embodiments, the subject is not concurrently being treated with a nutrition supplement prior to the administration of step i). In some embodiments of the methods provided herein, the subject is not concurrently being treated with a parenteral nutrition supplement prior to the administration of step i). In some embodiments of the methods provided herein, the subject has not been treated with a nutrition supplement within about 24 hours to about 1 week prior to the administration of step i), for example, within about 24 hours to about 1 week, about 24 hours to about 5 days, about 24 hours to about 4 days, about 24 hours to about 3 days, or about 24 hours to about 2 days. In some embodiments of the methods provided herein, the subject has not been treated with a nutrition supplement within about 24 hours prior to the administration of step i).

The present application further provides a method of reducing RES clearance of a nanotherapeutic agent from a subject in the treatment of a disease, the method comprising (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered; and the nanotherapeutic agent is a dichloro(1,2-diaminocyclohexane)platinum(II)/hyaluronic acid polymer (DACHPt/HANP) coated nanotherapeutic agent.

The present application further provides a method of improving the bioavailability of a nanotherapeutic agent in a subject in the treatment of a disease, the method comprising (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered; and the nanotherapeutic agent is a dichloro(1,2-diaminocyclohexane)platinum(II)/hyaluronic acid polymer (DACHPt/HANP) coated nanotherapeutic agent.

The present application further provides a method of reducing liver toxicity, spleen toxicity, and kidney toxicity of a nanotherapeutic agent in a subject in the treatment of a disease, the method comprising (i) administering Intralipid® 20% to the subject at a dose of about 2 g/kg and (ii) administering a therapeutically effective amount of the nanotherapeutic agent to the subject, wherein:

the Intralipid® 20% is administered about 1 hour before the nanotherapeutic agent is administered;

the nanotherapeutic agent is a dichloro(1,2-diaminocyclohexane)platinum(II)/hyaluronic acid polymer (DACHPt/HANP) coated nanotherapeutic agent.

In some embodiments, the nutrition supplement and the nanotherapeutic agent are administered to the subject in separate dosage forms.

In some embodiments, the methods provided herein further comprise monitoring the subject to determine if, for example, treatment with the nanotherapeutic agent results in an improvement of the disease for which the subject is being treated. In some embodiments, the monitoring comprises imaging the subject with an imaging technique. In some embodiments, the monitoring comprises obtaining a biological sample from the subject and analyzing the biological sample using an imaging technique. Example biological samples include, but are not limited to, blood, plasma, serum, urine, or tissue samples. Example imaging techniques include, but are not limited to, magnetic resonance imaging, optical imaging, single-photon emission computed tomography, positron emission tomography imaging, positron emission tomography with computed tomography imaging, positron emission tomography with magnetic resonance imaging, Cerenkov imaging, and ultrasound imaging.

Kits

The present application further provides a kit comprising one or more nutrition supplements provided herein and one or more nanotherapeutic agents provided herein. In some embodiments, the kit is for use in the treatment of a disease in a subject, wherein said kit comprises a nutrition supplement provided herein and a nanotherapeutic agent provided herein. In some embodiments, the disease is a disease provided herein (e.g., an autoimmune disease, an inflammatory disease, a fungal infection, or a cancer). In some embodiments, the nutrition supplement of the kit is to be administered to the subject from about 0.1 hours to about 24 hours before the nanotherapeutic agent is to be administered to the mammal. In some embodiments, the kit further comprises instructions for using the kit. In some embodiments, the instructions comprise instructions for administering the nutrition supplement and nanotherapeutic agent. In some embodiments, the instructions comprise instructions for performing a method provided herein. In some embodiments, the instructions comprise instructions for preparing a nutrition supplement provided herein. In some embodiments, the instructions comprise instructions for preparing a nanotherapeutic agent provided herein. The present application further provides methods for combining one or more nutrition supplements and one or more nanotherapeutic agents within a kit (e.g., in separate packages) for administration to a subject in the treatment of a disease (e.g., for sequential administration to the subject).

In some embodiments, the kit comprises:

i) one or more nutrition supplements provided herein;

ii) one or more nanotherapeutic agents provided herein; and iii) instructions for performing one or more of the methods provided herein.

In some embodiments, the kit comprises one nutrition supplement provided herein. In some embodiments, the kit comprises one nanotherapeutic agent provided herein.

In some embodiments, the kit comprises:

i) Intralipid® 20%;

ii) a nanotherapeutic agent comprising a chemotherapeutic agent and a hyaluronic acid polymer coated nanoparticle; and iii) instructions for administering the Intralipid® 20% from about 0.1 to about 24 hours before the nanotherapeutic agent is administered.

In some embodiments, the kit comprises:
i) Intralipid® 20%;
ii) a nanotherapeutic agent comprising a chemotherapeutic agent and a hyaluronic acid polymer coated nanoparticle; and
iii) instructions for administering the Intralipid® 20% about 1 hour before the nanotherapeutic agent is administered.

In some embodiments, the kit comprises:
i) Intralipid® 20%;
ii) a nanotherapeutic agent comprising a platinum-containing chemotherapeutic agent and a hyaluronic acid polymer coated nanoparticle; and
iii) instructions for administering the Intralipid® 20% from about 0.1 hours to about 24 hours before the nanotherapeutic agent is administered.

In some embodiments, the kit comprises:
i) Intralipid® 20%;
ii) a nanotherapeutic agent comprising a platinum-containing chemotherapeutic agent and a hyaluronic acid polymer coated nanoparticle; and
iii) instructions for administering the Intralipid® 20% about 1 hour before the nanotherapeutic agent is administered.

In some embodiments, the kit comprises:
i) Intralipid® 20%;
ii) a nanotherapeutic agent comprising oxaliplatin or dichloro(1,2-diaminocyclohexane)platinum(II) (DACHPt) and a hyaluronic acid polymer coated nanoparticle; and
iii) instructions for administering the Intralipid® 20% about 0.1 hours to about 24 hours before the nanotherapeutic agent is administered.

In some embodiments, the kit comprises:
i) Intralipid® 20%;
ii) a nanotherapeutic agent comprising oxaliplatin or dichloro(1,2-diaminocyclohexane)platinum(II) (DACHPt) and a hyaluronic acid polymer coated nanoparticle; and
iii) instructions for administering the Intralipid® 20% about 1 hour before the nanotherapeutic agent is administered.

In some embodiments, the kit comprises:
i) Intralipid® 20%;
ii) a nanotherapeutic agent comprising dichloro(1,2-diaminocyclohexane)platinum(II) (DACHPt) and a hyaluronic acid polymer coated nanoparticle; and
iii) instructions for administering the Intralipid® 20% about 0.1 hours to about 24 hours before the nanotherapeutic agent is administered.

In some embodiments, the kit comprises:
i) Intralipid® 20%;
ii) a nanotherapeutic agent comprising dichloro(1,2-diaminocyclohexane)platinum(II) (DACHPt) and a hyaluronic acid polymer coated nanoparticle; and
iii) instructions for administering the Intralipid® 20% about 1 hour before the nanotherapeutic agent is administered.

In some embodiments, the kit comprises:
i) one or more packages comprising a nutrition supplement provided herein (e.g., the Intralipid® 20%);
ii) one or more packages comprising a nanotherapeutic agent provided herein (e.g., dichloro(1,2-diaminocyclohexane)platinum(II) (DACHPt) and a hyaluronic acid polymer coated nanoparticle); and
iii) instructions for performing one or more of the methods provided herein.

In some embodiments, the kit comprises:
i) a first package comprising the nutrition supplement (e.g., the Intralipid® 20%);
ii) a second package comprising the nanotherapeutic agent (e.g., dichloro(1,2-diaminocyclohexane)platinum(II) (DACHPt) and a hyaluronic acid polymer coated nanoparticle); and
iii) instructions for performing one or more of the methods provided herein.

In some embodiments, the kit comprises:
i) a first package comprising Intralipid® 20%;
ii) a second package comprising a dichloro(1,2-diaminocyclohexane)platinum(II) (DACHPt) hyaluronic acid polymer nanotherapeutic agent; and
iii) instructions for administering the Intralipid® 20% about 0.1 hours to about 24 hours before the nanotherapeutic agent is administered.

In some embodiments, the kit comprises:
i) a first package comprising Intralipid® 20%;
ii) a second package comprising a dichloro(1,2-diaminocyclohexane)platinum(II) (DACHPt) hyaluronic acid polymer nanotherapeutic agent; and
iii) instructions for administering the Intralipid® 20% about 1 hour before the nanotherapeutic agent is administered.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. Suitable starting materials, synthetic methods, and assay methods may also be found, for example, in the disclosure of Liu et al, *Sci. Rep.* 2015, 5, 10881, the disclosure of which is incorporated by reference herein in its entirety.

General Methods and Materials
Materials and Animals

Intralipid® 20% was purchased from Fresenius Kabi (Bad Homburg, Germany). Dichloro(1,2-diamminocyclohexane)platinum(II) (DACHPtCl$_2$), AgNO$_3$, and the platinum (Pt) standard were purchased from Sigma-Aldrich (St. Louis, Mo.). Phosphate-buffered-saline (PBS) was obtained from Mediatech (Manassas, Va.).

Male Sprague Dawley (SD) rats with an indwelling jugular vein catheter implanted were purchased from Harlan Laboratories (Indianapolis, Ind.). All experiments involving animal subjects were approved by the Institutional Animal Care and Use Committee of Carnegie Mellon University. Animal care was provided in accordance with the Guide for the Care and Use of Laboratory Animals.

Experimental Design

Male SD rats, with body weights between 250 and 280 g, were used. Intralipid® 20% was administered by intravenous injection at a clinical dose of 2 g/kg. PBS was administered to control animals. After 1 h, DACHPt/HANP (2 mg Pt/kg for bioavailability and biodistribution studies, n=14 for Intralipid® pre-treatment group and n=14 for control group; 4 mg Pt/kg for toxicity studies, n=3 for Intralipid® pre-treatment group and n=3 for control group; 6 mg Pt/kg for another toxicity study to test the serum ALT activity and creatinine level, n=3 for Intralipid® pre-treatment group) was injected intravenously. Blood samples were collected at different time points to determine the bioavailability of DACHPt/HANP. At 5-, 24-, and 72-hr post injection of DACHPt/HANP, tissues (liver, spleen, and kidney) were collected for the Pt-level determination. The tissue samples collected at 72-hr post injection were used for histological analysis.

Blood Bioavailability

An indwelling jugular vein catheter was used for repeated blood samplings. Blood samples (100 μL) were collected at different time points to determine the changes of bioavailability of DACHPt/HANP upon Intralipid® treatment. Blood was sampled after DACHPt/HANP injection at 1, 5, 10, 20, 45, and 60 min, 3, 5, 24, 28, 48, 52, and 72 hr. The blood samples were decomposed in $HNO_3$ (0.5 mL) at 60° C. overnight and re-dissolved in 0.5 mL of 2 N HCl (see e.g., Cabral et al, *J. Control Release*, 2005, 101, 223-232; Oberoi et al, *Chemother. Res. Pract.* 2012, 905796; and Esteban-Fernandez et a, *J. Anal. Toxicol.* 2008, 32, 140-146). Suitable dilutions were prepared using 5% HCl to reach a final Pt concentration in the range of 0.02 to 1 part per million (ppm). Samples were analyzed for Pt concentration by inductively coupled plasma-mass spectrometry (ICP-MS) [NexION 300X (PerkinElmer, Waltham, Mass.)], with modified procedures from our previous studies (see e.g., Liu et al, *Biochim. Biophys. Acta.* 2013, 1830, 3447-3453; and International Patent Application No. WO 2014/039874, the disclosure of which is incorporated by reference herein in its entirety). $^{194}Pt$, $^{195}Pt$, and $^{196}Pt$ isotopes were analyzed and similar results were obtained from the measurement of these three isotopes. The Pt concentrations shown in this manuscript were calculated from the measurements of $^{194}Pt$. Bioavailability was calculated by the area under the curve (AUC), namely the integral of the concentration-time curve, using the trapezoidal rule with the use of KaleidaGraph 4.1 (Synergy Software, Reading, Pa.).

Pt Levels in Tissues

The wet weight of each tissue sample was recorded. Tissue homogenate (0.5 mL) was decomposed in $HNO_3$ (1 mL) at 60° C. overnight. The rest of the tissue was fixed in 4% paraformaldehyde for histological analyses. The $HNO_3$-digested samples were evaporated and then re-dissolved in 0.5 mL of 2 N HCl (see e.g., Esteban-Fernandez et a, *J. Anal. Toxicol.* 2008, 32, 140-146). The Pt concentrations in the solution were analyzed by ICP-MS as described above.

Pathological Analysis and TUNEL Assay

Histological examinations and TUNEL assays were performed by the Transplantation Pathology Laboratory of the University of Pittsburgh Medical Center (Pittsburgh, Pa.). Paraffin-embedded 5-μm sections were stained with H & E, or performed TUNEL staining. For histopathological diagnosis, slides were examined by light microscopy and photomicrographs were taken using a Moticam 2300 camera mounted on an Olympus Provis microscope with Mtic Images Plus 2.0 software.

ALT Activity Assay and Creatinine Colorimetric Assay

The activity of ALT in serum was measured by using the ALT Activity Assay Kit purchased from Sigma-Aldrich, according to the supplier's protocol. Serum creatinine level was measured by using the Creatinine Colorimetric/Fluorometric Assay Kit purchased from BioVision.

Statistical Analysis

Statistical analysis was carried out with Student's t test. A p value <0.05 was considered statistically significant.

Example 1. Preparation and Physical Properties of DACHPt/HANP

DACHPt/HANP was prepared with modified procedures from a previously described method (see e.g., Cabral et al, *J. Control Release*, 2005, 101, 223-232). In brief, $DACHPtCl_2$ was mixed with silver nitrate ($[AgNO_3]$/[DACHPt]=2) to form an aqueous complex. The solution was kept in the dark at 25° C. for 24 hr. AgCl precipitates were removed by centrifugation followed by filtration through a 0.22-μm hydrophilic polyvinylidene fluoride (PVDF) membrane (Millipore, Billerica, Mass.). Subsequently, HA/Boc-His/PEG graft copolymers, comprising hyaluronic acid (Mw=16 kD), were added to the aqueous complex of DACHPt at a 0.33 molar ratio of DACHPt to carboxylate groups of the HA modified polymers. The mixture was stirred in the dark for three days at 25° C. The reaction mixture was sonicated and then purified by ultrafiltration against deionized water to remove uncoordinated DACHPt. The product was filtered through a 0.22-μm PVDF membrane and lyophilized with 10% trehalose.

DACHPt/HANP exhibits an average hydrodynamic diameter of 150±30 nm, as determined by dynamic light scattering using a ZetaPlus (Brookhaven, Holtsville, N.Y.). The average Pt-core size is 19.1±6.2 nm, as measured by using a Cryo transmission electron microscope (Cryo-TEM) [JEM-2100 (JEOL, Tokyo, Japan)].

The particle size and PI of DACHPt/HANP was determined by dynamic light scattering using a ZetaPlus (Brookhaven, Holtsville, N.Y.). Zeta potential was measured by the laser Doppler anemometry (Zeta Plus zeta potential analyzer, Brookhaven Instruments Corporation).

TEM images were taken by using a Cryo transmission electron microscope (Cryo-TEM) [JEM-2100 (JEOL, Tokyo, Japan)] operated at 200 kV with attachment of energy dispersive spectroscopy (EDS). A droplet of DACHPt/HANP solution was adsorbed on a cleaned carbon film supported copper grid. After excess sample was removed, phosphotungstic acid (Merck) was used as negative stain reagent to improve the image contrast. TEM grid was dried in the contamination-free environment and reserved in the electronic dry cabinet for further TEM analysis.

In order to determine the encapsulation efficiency of DACHPt in the nanocomplex, the amount of Pt were quantified by inductively coupled plasma-optical emission spectrometry (ICP-OES) in preparation processes. Encapsulation efficiency (EE %) was calculated using below formula:

$$\text{Encapsulation efficiency (EE \%)} = (W_P/W_T) \times 100\%$$

where $W_P$ is the total amount of Pt after purification by passing through a 0.22 μm filter and $W_T$ is the total quantity of Pt determined before purification. The physical properties of DACHPt/HANP are shown below in Table 1.

TABLE 1

Physical Properties of DACHPt/HANP

| | Hydrodynamic Diameter (nm) | PI | Core Diameter (nm) | Zeta Potential pH 6.5 (mV) |
|---|---|---|---|---|
| DACHPt/HANP | 150 ± 30 | 0.24 ± 0.05 | 19.1 ± 6.2 | −17.9 ± 5.5 |

Example 2. Intralipid® Reduces Toxic Side Effects of Pt-Containing Nanotherapeutic Agents Intralipid® 20% was administered to rats at the clinical dose (2 g/kg) using the clinical route (i.e., intravenously) one hour before i.v. injection of DACHPt/HANP. At 24- and 72-hr post injection of DAHPt/HANP, blood samples were collected to determine serum alanine aminotransferase (ALT) activity and creatinine level to investigate liver and kidney damages. The tissue samples collected at 72-hr post injection were used for histological analysis.

Example 3. Pathological Analysis and Terminal Deoxynucleotidyl Transferase dUTP Nick End Labeling (TUNEL) Assay for Apoptotic Cells in Liver Light microscopic images of H & E stained liver tissue sections are shown in FIGS. 1A-C, 1F-1H, and 1K-1M. Images of TUNEL stained liver tissue sections are shown in FIGS. 1D-1E, 1I-1J, and 1N-1O. With DACHPt/HANP administration, but no Intralipid® pre-treatment, the pathological changes in the liver tissue are characterized by necrosis, as indicated by black arrows in FIG. 1C, which is an example of enlarged view from FIGS. 1A and 1B. Apoptotic cells are observed with TUNEL staining, as indicated by arrows in FIGS. 1D and 1E, from the liver tissue of this treatment group. An enlarged view of an apoptotic cell is shown as an example in FIG. 1E. These damages are significantly reduced upon Intralipid® pre-treatment. The liver tissue sections from the Intralipid® pre-treated group are shown in FIG. 1F-1J. Very few cell necroses (black arrow in FIG. 1H) and apoptotic cells (red arrows in FIG. 1J) were observed, comparable to the liver tissues of naïve rats (FIG. 1K-1O).

Example 4. Spleen Enlargement

Spleen swelling and enlargement were observed from DACHPt/HANP-treated animals, when the animals were sacrificed 72-h post nanotherapeutic agent administration, as shown in FIG. 2A, left vial). Intralipid® pre-treatment appears to reduce spleen swelling, as shown in FIG. 2A, right vial). The ratio of spleen weight/body weight for a naïve Sprague Dawley (SD) rat is 0.31±0.06 (n=3). Intralipid® treatment did not cause spleen swelling, with the ratio of 0.28±0.02 (n=3). The ratio from a DACHPt/HANP treated SD rat is 0.53±0.08 (n=3). Upon Intralipid® pre-treatment, this ratio reduces to 0.4±0.008 (n=3). In FIG. 2B, the ratios are shown as the percentage of the normal level.

Example 5. Pathological and TUNEL Assay Analyses of Spleen

Figures 3A, 3O:
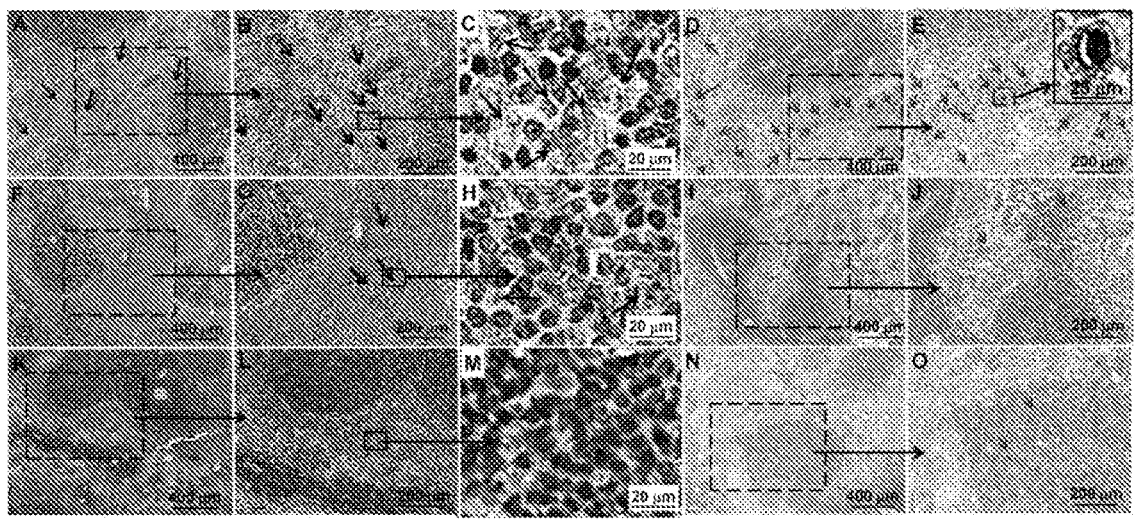
FIGS. 3A-3O show that Intralipid® 20% (clinical dose, 2 g/kg) reduces toxic side effects in spleen caused by DACHPt/HANP. Light microscopy images of H & E stained are shown in FIGS. 3A-3C, 3F-3H, and 3K-3M and TUNEL stained spleen tissue are shown in FIGS. 3D-3E, 3I-3J, and 3N-3O.

Light microscopy images of H & E stained (FIGS. 3A-3C, 3F-3H, and 3K-3M) and TUNEL stained (FIGS. 3D-3E, 3I-3J, and 3N-3O) spleen tissue sections are shown in FIG. 3. With DACHPt/HANP administration, but no Intralipid® pre-treatment, the pathological changes in the spleen tissue were characterized by concurrent abnormal proliferation of mononuclear cells as indicated by black arrows on FIG. 3A and necrosis as indicated by black arrows on FIGS. 3B-3C. Morphological changes and enlarged size were also observed. TUNEL staining of spleen tissue from DACHPt/HANP treatment revealed a large amount of apoptotic cells (FIGS. 3D and 3E). In contrast, uniformly distributed mononuclear cells (FIG. 3F), few necrotic (FIGS. 3G-3H), and few apoptotic (FIGS. 3I-3J) spleen cells were detected from the Intralipid® pre-treatment group, which is similar to that of naïve rats, as shown in FIGS. 3K-3O.

Example 6. Pathological and TUNEL Assay Analyses of Kidney

Figures 4A, 4B, 4C, 4D, 4E, 4F, 4G, 4H, 4I, 4J, 4K, 4L:
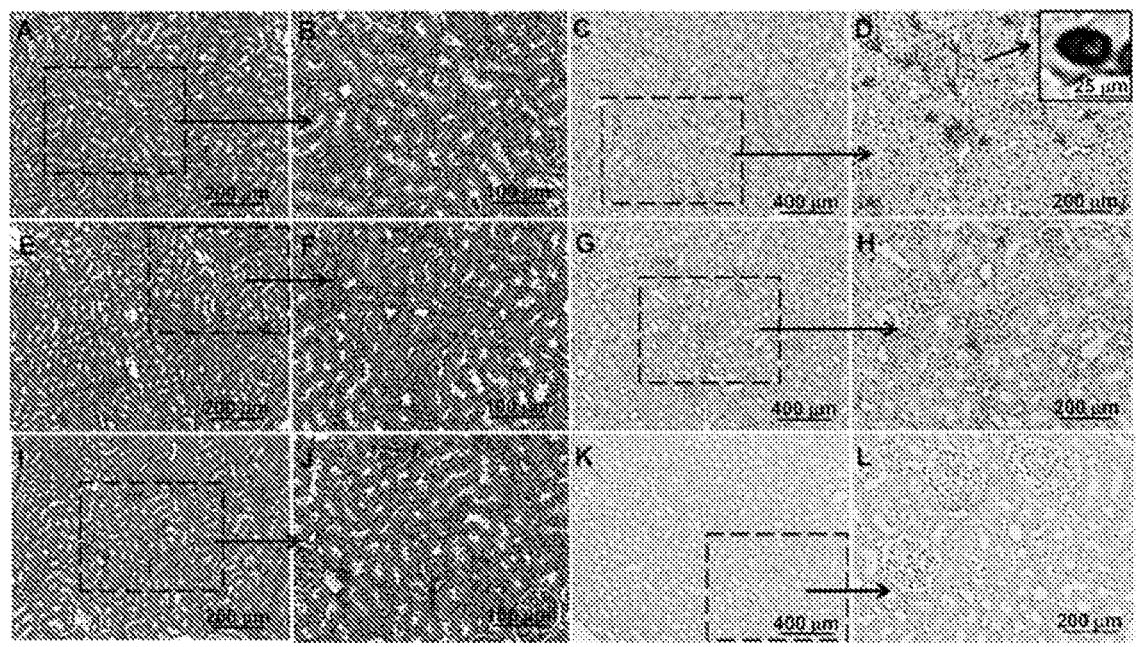
FIGS. 4A-4L show that Intralipid® 20% (clinical dose, 2 g/kg) reduces toxic side effects in kidney caused by DACHPt/HANP. Light microscopy images of H & E stained are shown in FIGS. 4A-4B, 4E-4F, and 4I-4J and TUNEL stained spleen tissue are shown in FIGS. 4C-4D, 4G-4H, and 4K-4L.

Intralipid® was found to protect kidney cells from the damage caused by the Pt-nanotherapeutic agent. With Intralipid® pre-treatment, the apoptotic cells in kidney, caused by the treatment of DACHPt/HANP, was decreased, as shown in FIGS. 4D vs 4H, arrows. Light microscopic images of H & E stained kidney tissue, with or without Intralipid® pre-treatment, look similar, as shown in FIGS. 4B and 4F).

Figures 5A, 5B, 5C, 5D:
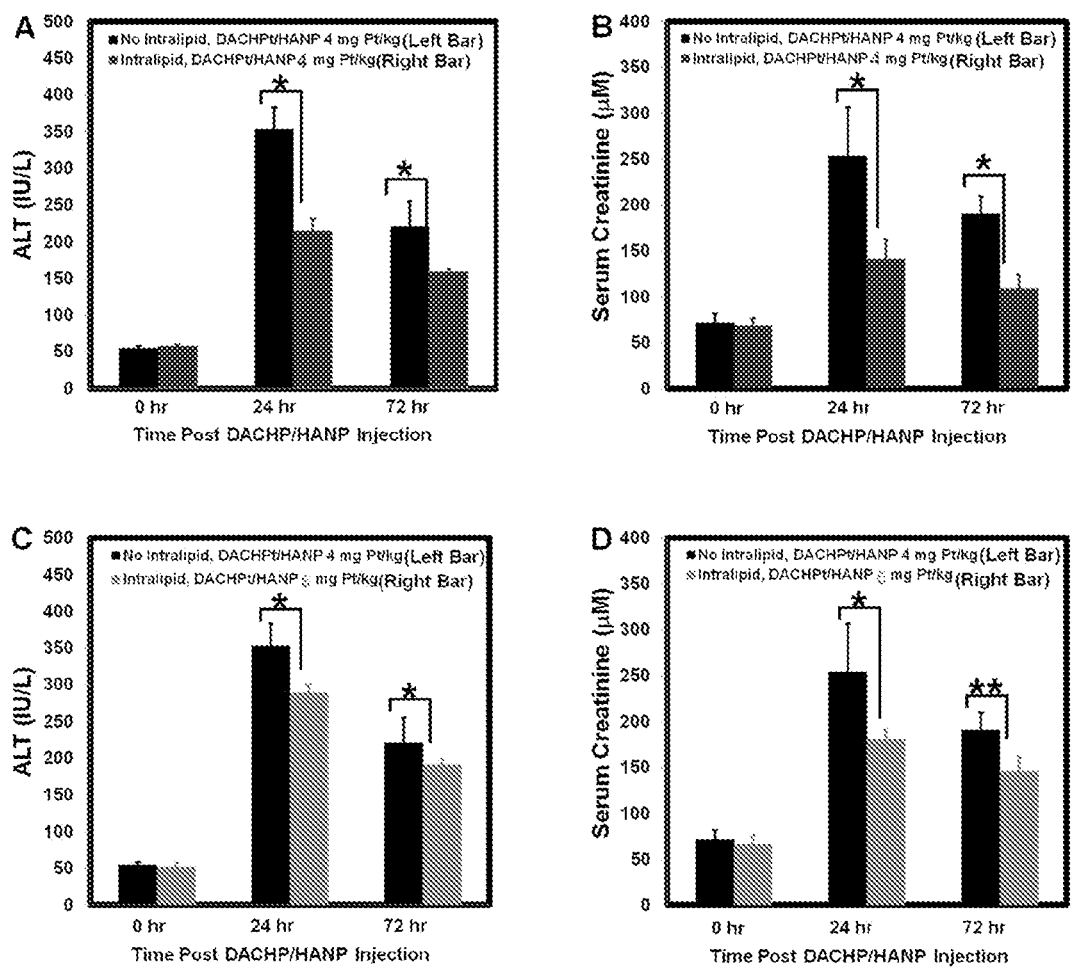
FIGS. 5A-5D show the effects of Intralipid® 20% (clinical dose, 2 g/kg) pre-treatment on serum alanine aminotransferase (ALT) activities (5A, 5C) and creatinine levels (5B, 5D) in DACHPt/HANP treated rats. When the rats are treated with 4 mg Pt/kg of the nanotherapeutic agent, the Intralipid® pre-treatment group shows significantly lower serum ALT activity and creatinine level (5A and 5B). The group, which is pre-treated with Intralipid® followed by the treatment of a higher dosage (6 mg Pt/kg) of DACHPt/HANP, exhibits lower ALT activity and creatinine level than the group, which is treated with 4 mg Pt/kg of the nanotherapeutic agent, but no Intralipid® (5C and 5D). *$p<0.001$; **$p<0.05$.

Example 7. ALT Activity and Creatinine Colorimetric Assays to Assess Liver and Kidney Damages The serum ALT activity is 54.4±3.3 IU/L for naïve rats. Intralipid® treatment did not alter ALT activity (57.1±2.2 IU/L, as shown in FIG. 5A). With no Intralipid® protection, the serum ALT activities were elevated to 353.2±29.9 IU/L and 220.4±34.9 IU/L at 24- and 72-hr post Pt-nanotherapeutic agent injection, respectively. With Intralipid® pre-treatment, serum ALT activities were 214.9±16.5 IU/L and 159.5±3.1 IU/L at 24 hr and 72 hr, indicating that Intralipid® reduces the hepatocellular damages from the Pt-nanotherapeutic agent. This result is consistent with the findings in the liver histological studies as shown in FIG. 1.

Consistent with the pathological findings in kidney (FIG. 4), Intralipid® 20% (clinical dose, 2 g/kg) pre-treatment also decreased serum creatinine level significantly, as shown in FIG. 5B). At 24- and 72-hr post DACHPt/HANP administration, the creatinine levels increased to 253.6±53.1 μM and 190.2±19.2 μM, respectively. With Intralipid® pre-treatment, the creatinine levels were 141.0±21.1 μM and 109.0±14.8 μM, respectively, indicating a reduction of the kidney damage.

To show the potency of this Intralipid® protective effects, the rats (n=3) were pre-treated with Intralipid® followed by a higher dosage, 6 mg Pt/kg, of DACHPt/HANP. At 24- and 72-hr post nanotherapeutic agent treatment, serum ALT activities were 289.2±11.3 IU/L and 191.5±6.9 IU/L, respectively; creatinine levels were 180.2±11.3 μM and 145.2±16.2 μM. These activities and levels were all significantly lower than the group treated with lower dosage of the nanotherapeutic agent (4 mg Pt/kg), but no Intralipid® pre-treatment, as shown in FIGS. 5C-5D).

Example 8. Changes of DACHPt/HANP Accumulation in Tissues Upon Intralipid® Pre-Treatment The Pt concentration in tissue (spleen, liver, and kidney) and blood of naïve animals or Intralipid® along or phosphate-buffered-saline (PBS) treated animals was below 0.01 part per million (ppm).

Example 9. DACHPt/HANP Accumulation in Liver

In a previous study (see e.g., Liu et al, *Biochim. Biophys. Acta*, 2013, 1830, 3447-3453), it was found that in rodents, Intralipid® reduces RES uptake by ~50% of nano- and micron-sized particles in which MRI contrast agents are loaded. The RES plays an important role in the uptake and metabolism of Intralipid® (see e.g., Vilaro et al, *J. Nutr.* 1988, 118, 932-940; and Fraser et al, *J. Leukoc. Biol.* 1984, 36, 647-649). The blood half-life of Intralipid® 20% (clinical dose 2 g/kg) administered by intravenous bolus in rats is 8.7±3.0 min. The diameter of the Intralipid® particles range from 200 to 1000 nm. As shown in FIGS. 6A-6B, Intralipid® pre-treatment decreased the liver and spleen uptake of the nanotherapeutic agent by 20.4% and 42.5% at 24-hr post nanotherapeutic agent administration, respectively.

With DACHPt/HANP administration, the Pt concentrations in liver were 8.6±0.6 and 18.1±2.2 (μg/g wet weight) at 5- and 24-hr post injection, as shown in FIG. $6A_1$. These translate into 81.6±5.9 and 179.0±11.2 μg Pt in the liver, as shown in FIG. $6A_2$. With Intralipid® pre-treatment, the Pt concentrations in the liver decreased to 6.6±0.5 and 13.9±1.6 (μg/g wet weight) at 5- and 24-hr post DACHPt/HANP injection, as shown in FIG. $6A_1$. The total amounts of Pt decrease to 61.2±4.2 and 142.5±18 μg, as shown in FIG. $6A_2$. Thus, one single administration of Intralipid® significantly decreased liver accumulation of the nanotherapeutic agent by 24.9% and 20.4% at 5- and 24-hr post injection, respectively.

With the drug being metabolized in the liver, the Pt concentrations reached similar level at 72 hr: 10.1±1.6 and 11.8±3.7 (μg/g wet weight), without- and with-Intralipid® pre-treatment, respectively.

Example 10. DACHPt/HANP Accumulation in Spleen

FIGS. $6B_1$ and $6B_2$ show the changes in the spleen accumulation of the DACHPt/HANP upon Intralipid® pre-treatment. With DACHPt/HANP administration, the Pt concentrations in spleen were 6.9±1.2, 26.2±2.5, and 16.9±2.9 (μg/g wet weight) at 5-, 24-, and 72-hr post injection, respectively, as shown in FIG. $6B_1$. These translate into 4.9±0.9, 18.3±1.8, 24.2±4.4 μg Pt in spleen, respectively, as shown in FIG. $6B_2$. With Intralipid® pre-treatment, the Pt concentration in the spleen decreased to 4.2±0.6, 15.3±1.2, and 7.3±1.6 (μg/g wet weight), respectively, as shown in FIG. $6B_1$ and the total amount of Pt in the spleen decreased to 2.9±0.4, 10.6±0.8, and 7.9±1.9 μg, respectively at these three time points, as shown in FIG. $6B_2$. Thus, one single administration of Intralipid® significantly decreased spleen uptake of the nanotherapeutic agent by 40.1%, 42.4, and 67.2% at 5-, 24-, and 72-hr post administration.

Example 11. DACHPt/HANP Accumulation in Kidney

We have observed that the Pt accumulations in kidney also decreased upon Intralipid® pre-treatment, as shown in FIGS. $6C_1$ and $6C_2$. Nephrotoxicity is one of the most severe side effects of current Pt drugs. DACHPt/HANP nanotherapeutic agent is designed to increase the concentration and prolong the half-life of DACHPt at tumor sites and to decrease the side effects like nephrotoxicity. In addition to the Intralipid® therapy decreasing the RES uptake of the nanotherapeutic agent, Intralipid® pre-treatment also decreased the Pt drug (DACHPt and/or DACHPt/HANP) accumulation in kidney by 28.7% at 72 hr.

With no Intralipid® pre-treatment, the Pt concentration in kidney was 4.9±0.3, 6.1±1.5, and 7.9±1.4 (μg/g wet weight) at 5-, 24- and 72-hr post DACHPt/HANP injection, as shown in FIG. $6C_1$. These translate into 9.7±0.6, 13.5±3.8, and 15.1±3.7 μg Pt in kidney, as shown in FIG. $6C_2$. With Intralipid® pre-treatment, the Pt concentrations in kidney decreased to 3.2±0.5, 4.2±0.5, and 5.9±0.7 (μg/g wet weight), as shown in FIG. $6C_1$ and total amounts of Pt in kidney decreased to 6.4±1.0, 9.3±0.4, and 10.8±1.7 μg, as shown in FIG. $6C_2$ at 5-, 24- and 72-hr post DACHPt/HANP injection. Thus, Intralipid® pre-treatment significantly decreased the Pt drug accumulation in the kidney by 34.0, 31.2, and 28.7% at 5-, 24-, and 72-hr post DACHPt/HANP administration, respectively.

Example 12. Blood Clearance and Bioavailability

The method described herein with Intralipid® pre-treatment changes the clearance and increases the bioavailability of the nanotherapeutic agent. The results show that a single dose of Intralipid® increased the bioavailability of DACHPt/HANP by 18.7% during the first 5 hr, as shown in FIG. 7. It has been reported that after intravenous (i.v.) administration of Intralipid®, the circulating ketone bodies increased ~100% in 30 min, which indicates an active metabolism of Intralipid® by the liver (see e.g., Vilaro et al, *J. Nutr.* 1988, 932-940). Without being bound by theory, this active metabolism may explain the decrease of the effectiveness of Intralipid® after 5 hr. This method is generally applicable to varying administration routes, dosages, and time courses of Intralipid®.

Changes in the Pt concentrations in blood upon Intralipid® pre-treatment are shown in FIG. 7. The bioavailability of the Pt-drug is calculated by the area under the curve (AUC), namely the integral of the Pt concentration-time curve, using the trapezoidal rule. A single administration of Intralipid® increased the bioavailability of the Pt drug by 18.7% during the first 5 hr ($p<0.0001$) and by 9.4% during 24 hr ($p<0.001$), as shown in FIG. 8. This finding indicates that Intralipid® can change the clearance and increase the bioavailability of the nanotherapeutic agent.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer in a subject in need thereof, comprising (i) administering to the subject a fat emulsion comprising 20% soybean oil, 1.2% egg yolk, and 2.25% glycerol; and (ii) administering a therapeutically effective amount of a nanotherapeutic agent to the subject, wherein the nanotherapeutic agent comprises a therapeutic agent and a nanocarrier, wherein the nanocarrier is selected from the group consisting of a protein-coated nanoparticle and a polymer-coated nanoparticle; wherein said fat emulsion is administered to the subject about 0.5 hours to about 2 hours before the nanotherapeutic agent is administered to the subject;

wherein the cancer is selected from the group consisting of breast cancer, prostate cancer, esophageal cancer, liver cancer, colon cancer, testicular cancer, endometrial cancer, brain cancer, bladder cancer, cancer of the uterus, cancer of the ovary, cervical cancer, lung cancer, sarcoma, bone cancer, pancreatic cancer, renal cancer, stomach cancer, and cancer of the head and neck;

wherein the therapeutic agent is dichloro(1,2-diaminocyclohexane)platinum(II);

wherein toxic side effects to the liver, kidney, or spleen are reduced as compared with a method of administration of the nanotherapeutic agent without pre-administration of the fat emulsion, and wherein either serum alanine aminotransferase (ALT) or serum creatinine levels are significantly reduced as compared with a method of administration of the nanotherapeutic agent without pre-administration of the fat emulsion.

2. The method of claim 1, wherein clearance of the nanotherapeutic agent from the subject is reduced as compared with a method of administration of the nanotherapeutic agent without pre-administration of the fat emulsion.

3. The method of claim 2, wherein reticuloendothelial system (RES) clearance of the nanotherapeutic agent from the subject is reduced as compared with a method of administration of the nanotherapeutic agent without pre-administration of the fat emulsion.

4. The method of claim 1, wherein the bioavailability of the nanotherapeutic agent in the subject in the treatment of the cancerous disease is improved as compared with a method of administration of the nanotherapeutic agent without pre-administration of the fat emulsion.

5. The method of claim 1, wherein the nanotherapeutic agent further comprises a hyaluronic acid polymer coating.

6. The method of claim 5, wherein the fat emulsion is administered about 1 hour before the nanotherapeutic agent is administered.

7. The method of claim 1, wherein accumulation of the nanotherapeutic in the liver is decreased by about 10% to about 30% compared to accumulation of the nanotherapeutic agent in the liver without pre-administration of the fat emulsion.

8. The method of claim 7, wherein accumulation of the nanotherapeutic in the liver is decreased by about 15% to about 25% compared to accumulation of the nanotherapeutic agent in the liver without pre-administration of the fat emulsion.

9. The method of claim 1, wherein accumulation of the nanotherapeutic agent in the spleen is decreased by about 25% to about 50% compared to accumulation of the nanotherapeutic agent in the spleen without pre-administration of the fat emulsion.

10. The method of claim 9, wherein accumulation of the nanotherapeutic agent in the spleen is decreased by about 35% to about 45% compared to accumulation of the nanotherapeutic agent in the spleen without pre-administration of the fat emulsion.

11. The method of claim 1, wherein accumulation of the nanotherapeutic agent in the kidney is decreased by about 5% to about 15% compared to accumulation of the nanotherapeutic agent in the kidney without pre-administration of the fat emulsion.

12. The method of claim 11, wherein accumulation of the nanotherapeutic agent in the kidney is decreased by about 6% to about 12% compared to accumulation of the nanotherapeutic agent in the kidney without pre-administration of the fat emulsion.

13. The method of claim 4, wherein bioavailability of the nanotherapeutic agent is improved by about 5% to about 20% compared to the bioavailability of the nanotherapeutic agent without pre-administration of the nutrition supplement.

\* \* \* \* \*